United States Patent [19]

Matthews et al.

[11] Patent Number: 5,451,516
[45] Date of Patent: Sep. 19, 1995

[54] BIFUNCTIONAL PROTEIN FROM CARROTS (DAUCUS CAROTA) WITH ASPARTOKINASE AND HOMOSERINE DEHYDROGENASE ACTIVITIES

[76] Inventors: Benjamin F. Matthews, 8708 Crystal Rock La., Laurel, Md. 20708; Jane M. Weisemann, 310 Souder Rd., Brunswick, Md. 21716

[21] Appl. No.: 746,705

[22] Filed: Aug. 16, 1991

[51] Int. Cl.⁶ ............... C12N 15/53; C12N 15/54; C12N 15/63
[52] U.S. Cl. ............... 435/190; 435/69.1; 435/194; 435/172.3; 435/320.1; 435/252.3; 536/23.2; 935/14; 935/29; 935/56
[58] Field of Search ............ 435/69.1, 320.1, 252.3, 435/190, 194, 172.3; 536/23.2; 935/14, 29, 56

[56] References Cited
PUBLICATIONS

Dotson et al., *Plant Physiol.*, vol. 93, pp. 98–104 (1990).
Turano et al., *Plant Physiol.*, vol. 92, pp. 395–4000 (1990).
Dotson et al., *Plant Physiol.*, vol. 91, pp. 1602–1608 (1989).
Matthews et al., *Plant Physiol.*, vol. 91, pp. 1569–1574 (1989).
Krishnaswamy et al., *Archives of Biochemistry and Biophysics*, vol. 227(1), pp. 210–224 (Nov., 1983).
Krishnaswamy et al., *Archives of Biochemistry and Biophysics*, vol. 222(2), pp. 449–463 (15 Apr. 1983).
Matthews et al., *Z. Pflanzenphysiol.*, vol. 96(5), pp. 453–463 (1980).
Walter et al., *The Journal of Biological Chemistry*, vol. 254(4) pp. 1349–1355 (25 Feb. 1979).
Matthews et al., *Canadian Journal of Botany*, vol. 57(4), pp. 299–304 (15 Feb. 1979).
Matthews et al., *Z. Naturforsch*, vol. 34, pp. 1177–1185 (1979).
Matthews et al., *Phytochemistry*, vol. 18, pp. 395–399 (1979).
Matthews et al., *Planta*, vol. 141, pp. 315–321 (1978).
Bryan et al., *Plant Physiol.*, vol. 59, pp. 673–679 (1977).
Matthews et al., *Plant Physiol.*, vol. 55, pp. 991–998 (1975).
B. F. Matthews et al. "Cloning an mRNA Encoding the Bifunctional Enzyme . . . " Plant Physiology 96(1) 126 Abst. #847 (May 1991).
B. F. Matthews et al "Cloning of a cDNA Encoding Homoserine Dehydrogen as . . . " Plant Physiology 93(1) 42 Abstr #234 (May 1990).
S. L. Berger et al. "Guide to Molecular Cloning Techniques". Meth. in Enzymol. vol. 152 pp. 393–399, 415–423, 432–447, 661–704 (1987).

*Primary Examiner*—Robert A. Wax
*Assistant Examiner*—Rebecca Prouty
*Attorney, Agent, or Firm*—Janelle S. Graeter; M. Howard Silverstein; John Fado

[57] ABSTRACT

An isolated and purified bifunctional protein from carrots with aspartokinase and homoserine activities which can be used to regulate the amino acid content of plants, in particular the lysine, homoserine, threonine, isoleucine and/or methionine content is disclosed. In addition, a DNA molecule with a DNA sequence coding for a homologous segment of the bifunctional carrot protein is also disclosed. In a method of regulating the amino acid content in a plant by bringing an effective amount of the bifunctional protein in contact with the plant is disclosed.

10 Claims, 24 Drawing Sheets

| Fig. 8A |
|---|
| Fig. 8B |
| Fig. 8C |
| Fig. 8D |
| Fig. 8E |
| Fig. 8F |

Fig. 8

```
  1
  G GAG TCG TCG TCG AAG TTT TAC ATT GCT TCC GTT ACA ACT GCA GTT CCT TCT
    E   S   S   S   K   F   Y   I   A   S   V   T   T   A   V   P   S
                                                        100          50

CTC GAT GAC TCC GTT GAG AAG CAC CTT CCC AGG GCT ATG TGG TCT ATT CAT
   L   D   D   S   V   E   K   H   L   P   R   A   M   W   S   I   H

AAA TTT GGA GGC ACC TGT GTG GGA AGC TCT GAA AGG ATC CGA GGT GCT AAT GTT GCA GAG ATA
   K   F   G   G   T   C   V   G   S   S   E   R   I   R   G   A   N   V   A   E   I
                                             200             150

GTT GTG GAG GAT GAT TCT GAA CTA GTT GTA AGA AAG CTA TAC AAG GCG CAG TCA GTC TCT ATG TCA AAG GTC
   V   V   E   D   D   S   E   L   V   V   R   K   L   Y   K   A   Q   S   V   S   M   S   K   V
                                                 250

ACA GAT ATG TAT GAT CTA ATT ATG GAA AAG CAC AGG CTG GGT CAT TTA ACA CAG CAA TCA CGG GAT TCT TAT GAA
   T   D   M   Y   D   L   I   M   E   K   H   R   L   G   H   L   T   Q   Q   S   R   D   S   Y   E
                        300

TCT GCG CTC GAT GCT GTT ATG AGA TTT TTA ACT AGG CTG CAT GCC ACC GAA TCT TTT GAT CTC CTT GAT
   S   A   L   D   A   V   M   R   F   L   T   R   L   H   A   T   E   S   F   D   L   L   D
                  350                                                             500

GGA GAT GAC CTT CGT GCT GCA ATA TAC ATA GCT GCT CAG CTG TTG TCA GTT CTT AAC AAC CTC AAA
   G   D   D   L   R   A   A   I   Y   I   A   A   Q   L   L   S   V   L   N   N   L   K
  400                                                                                 450

GCA ATG CTT CGT GGA CAT GGA GAG CTA TGG TCA TCA GCT CAG CTG TTG TCA GAT CTT TAT GAT AGA AAG
   A   M   L   R   G   H   G   E   L   W   S   S   A   Q   L   L   S   D   L   Y   D   R   K

GTT GTG GGA GAT CAT CTT CGT GGA GAG CTA TGG TCA TGG CTG TCA GTT CTT GAT GTT GTA ATA AAT CCT GCT
   V   V   G   D   H   L   R   G   E   L   W   S   W   L   S   V   L   D   V   V   I   N   P   A
                                                                   550

AAT GGG GGT GAC TGT GAT ATG GAC ACA CGA GAT GTT GTT CTT GTA AAT CCT GCT
   N   G   G   D   C   D   M   D   T   R   D   V   V   L   V   N   P   A
```

Fig. 8A

```
GGA TCT AAT CAA GTC GAT CCT GAT TAT TTG GAA TCT GAG AAG AGA CTT GAG AAA TGG
 G   S   N   Q   V   D   P   D   Y   L   E   S   E   K   R   L   E   K   W
                                    600

TTC TCC AGC AAC CAG TGT CAG ACA ACT TTG AAA AGA GAC GTC CAA ATT GTT GCG ACA GGT TTT ATA GCT AGC ACG CCT
 F   S   S   N   Q   C   Q   T   T   L   K   R   D   V   Q   I   V   A   T   G   F   I   A   S   T   P
                     650                              700

CAA AAT ATA CCT ACA ACT TTG AGG GCT GGT CAA GTC ACG ATT TGG ACT GAT GTT AAT GGT TTT TCT GCC ATA ATG
 Q   N   I   P   T   T   L   R   A   G   Q   V   T   I   W   T   D   V   N   G   F   S   A   I   M
             750                                    800

GGT GCT TTA AGG GCT GGT CAA GTC ACG ATT TGG ACT GAT GTT AAT GGT
 G   A   L   R   A   G   Q   V   T   I   W   T   D   V   N   G

AGT GCA GAT CCT CGA AAA GTT AGT GAG GCT GTG GTA TTA AAG ACA TTG TCT TAT CAA GTA TAT
 S   A   D   P   R   K   V   S   E   A   V   V   L   K   T   L   S   Y   Q   V   Y
                                                                PEP.76             850

GAA GCC TGG GAG ATG TCA TAT TTT GGG GCT AAT GTG TTA CAT CCC CGT ACT CCC ATC ATT
 E   A   W   E   M   S   Y   F   G   A   N   V   L   H   P   R   T   P   I   I
                                                    900           950

CCT GTG ATG CGA TAT GAC ATT CCA ATT GTA ATA AGA AAT ATA TTC AAC CTA TCT GCT
 P   V   M   R   Y   D   I   P   I   V   I   R   N   I   F   N   L   S   A
                                            1000

CCG GGA ACA ATG ATA TGC CGA GAA TCT GTA GGC GAA ACT GAA GAT GGG TTA AAA TTG
 P   G   T   M   I   C   R   E   S   V   G   E   T   E   D   G   L   K   L
```

```
GAA TCT CAT GTC AAA GGA TTT GCT ACT ATT AAT GTT GAA
 E   S   H   V   K   G   F   A   T   I   N   V   E
            PEP.90                1050

GGA ACT GGA ATG GCT GGT CCT GTT ACA GCT AGT GCA ATT TTT GGT GCT GTC AAG
 G   T   G   M   A   G   P   V   T   A   S   A   I   F   G   A   V   K
                     1100                        1150              [S]  (K)

GAT GTG GGA GCT AAT GTT ATA ATG AAA GTT GAA AGT GCA TCT CAG AGC AGT GAG CAT ATT TGC
 D   V   G   A   N   V   I   M   K   V   E   S   A   S   Q   S   S   E   H   I   C
         1200                                                    1250

TTT GCT GTG CCT GAG AGT GAT GCT TTA GAT GCT GTT TCC CAG GTT ACT CCT GCT ATA GCC TTG GAG GCC AGA
 F   A   V   P   E   S   D   A   L   D   A   V   S   Q   V   T   P   A   I   A   L   E   A   R

CGT CAA GCT ACA GTT CCT GAG GTT CTT GCA ATG GCA AAT ATA AAC GTT CGA GAA ACA ACA ATA GCA GTG GGA
 R   Q   A   T   V   P   E   V   L   A   M   A   N   I   N   V   R   E   T   T   I   A   V   G
                                    1300                        1350                    1400

ATC TTG GCA ACA GTT GGC CAA AAG ATG ATA AAC GTT CTC AGT CGA ACC ACA ATA GCA GTG GGA ATT GTC GGA
 I   L   A   T   V   G   Q   K   M   I   N   V   L   S   R   T   T   I   A   V   G   I   V   G

TTC AAT ATC ACT GCA AAG GCC AAT ATA AAC GTT CTC AGT CGA ACC ACA ATA GCA GTG GGA ATT GTC GGA CCT
 F   N   I   T   A   K   A   N   I   N   V   L   S   R   T   T   I   A   V   G   I   V   G   P
                                            1450                                1500

GAG TAT AAT ATC ACT GTA GTT CTC AGT CGA GAA GAT TGT GTG AGG GCT TTG AAA GCT
 E   Y   N   I   T   V   V   L   S   R   E   D   C   V   R   A   L   K   A

GTC CAT TCA AGA TTT TAT CTG TCG AGA ACC ACA ATA GCA GTG GGA ATT GTC GGA CCT
 V   H   S   R   F   Y   L   S   R   T   T   I   A   V   G   I   V   G   P
```

Fig. 8D

```
GGA TTA ATC GGA GCT ACT TTA CTT GAC CAG CTC AGG GAT CAG GCA GCA ATC CTC AAG
 G   L   I   G   A   T   L   L   D   Q   L   R   D   Q   A   A   I   L   K
             1550                                                      1650

GAA AAT TCT AAA ATT GAT TTG CGT GTT ATG GGT ATC ACC GGA TCG GCA ACA ATG CTT
 E   N   S   K   I   D   L   R   V   M   G   I   T   G   S   A   T   M   L
     1600                                                  1700

CTG AGC GAA ACG GGA ATC GAT TTA AGT AGA TGG AGA GAA GTC CAA AAA GAG AAA GGG
 L   S   E   T   G   I   D   L   S   R   W   R   E   V   Q   K   E   K   G
                                                     1750

CAA ACA GCT GGC CTA GAA AAA TTT GTA CAA CAT GTG CGT GGA AAT CAT TTT ATT CCA
 Q   T   A   G   L   E   K   F   V   Q   H   V   R   G   N   H   F   I   P
                                             1800

AGC ACT GTT ATA GAT TGT ACA GCA GAC TCT GAA CAT GTG CGT GGA... 
```

*(Partial transcription — PEP. 97 underlined region noted near position 1800)*

Fig. 8D

| | | | | | | | | | | | | | | | | |
|---|---|---|---|---|---|---|---|---|---|---|---|---|---|---|---|---|
| GAA | ACC | GGG | GAC | AAG | ATA | TTG | CGA | ATT | GAA | GGC | ATT | TTC | AGT | GGG | ACT | CTT | AGT | TAC |
| E | T | G | D | K | I | L | R | I | E | G | I | F | S | G | T | L | S | Y |
| | | 2000 | | | | | | | | | | | | | 2100 | | | 2050 |

| ATA | TTC | AAC | AAC | TTT | ACT | GAA | CCA | ACA | CCT | TTT | AGT | GAA | GTG | GTA | AGT | GGA | GAG | GCA | AAA |
|---|---|---|---|---|---|---|---|---|---|---|---|---|---|---|---|---|---|---|---|
| I | F | N | N | F | T | E | P | T | P | F | S | E | V | V | S | G | E | A | K |

2150

| GCG | GCA | GGG | TAT | ACT | GAA | CCA | GAT | CCA | AGG | GAT | CCA | AGG | GAT | CTA | GCC | GGA | ACT | GAT | GTT | GCT |
|---|---|---|---|---|---|---|---|---|---|---|---|---|---|---|---|---|---|---|---|---|
| A | A | G | Y | T | E | P | D | P | R | D | L | A | G | T | D | V | A |

2200

| AGA | AAG | GTA | ATA | ATT | CTT | GCT | AGA | GAA | TCT | GGA | TTA | AAG | CTC | GAA | TCT | GAT | ATC |
|---|---|---|---|---|---|---|---|---|---|---|---|---|---|---|---|---|---|
| R | K | V | I | I | L | A | R | E | S | G | L | K | L | E | S | D | I |

2250

| CCT | GTA | CAG | AGC | CTT | GTT | CCA | GAA | CCA | CTA | AGG | GGT | ATT | GCG | TCA | GCC | GAA | GAA | TTT |
|---|---|---|---|---|---|---|---|---|---|---|---|---|---|---|---|---|---|---|
| P | V | Q | S | L | V | P | E | P | L | R | G | I | A | S | A | E | E | F |

2300

| CTG | CTA | CAG | CTA | CCA | CAG | TTT | GAT | TCA | GAT | ATG | GTG | GTG | GGG | GTG | GAT | GCC | GTA | AAT | CAA | AAA | GGT |
|---|---|---|---|---|---|---|---|---|---|---|---|---|---|---|---|---|---|---|---|---|---|
| L | L | Q | L | P | Q | F | D | S | D | M | V | V | G | V | D | A | V | N | Q | K | G |

2350

| AAT | GCA | GGG | GAA | GTT | CTA | AAA | AGA | TAC | AAG | AAA | GAG | CAC | CCG | TTC | GCA | CAG | CTT | TCT | GGG | TCC |
|---|---|---|---|---|---|---|---|---|---|---|---|---|---|---|---|---|---|---|---|---|
| N | A | G | E | V | L | K | R | Y | K | K | E | H | P | F | A | Q | L | S | G | S |

| GTT | GTT | GAA | TTG | AAA | AGA | TAC |
|---|---|---|---|---|---|---|
| V | V | E | L | K | R | Y |

```
2450                                                                            2500
GAT AAC ATC ATT GCT TTC ACA ACT GAA AGA TAC AAC AAG CAA CCT CTT ATA ATT CGA
 D   N   I   I   A   F   T   T   E   R   Y   N   K   Q   P   L   I   I   R
                                                 2550
GGT CCT GGT GCT GGG GCA GAG GTG ACA GCT GGT GGA GTA TTC AGT GAT ATT TTG CGG
 G   P   G   A   G   A   E   V   T   A   G   G   V   F   S   D   I   L   R
                                     2600
CTT GCT TCA TAT CTT GGT GCA CCA TCA TAA TCCATTAGTTGAGCTCTCAATGTTTACCCTTTGT
 L   A   S   Y   L   G   A   P   S   *
PEP.33 L A  S   Y   L   G   A   P   S
                   2650                                                 2700
CAGCCCAAATTATGTTATAGAATTTAGGGAGCTTTGCCTATTATTAGGTTAGTATCAAAACATTCTTCTACGCT
                                          2750
GCATAAGAGAACACTTCATGCAATTTGGGTTTCTTTAGTGGCTTTCTAGCCAACCCAAATGTGTCATAGTCTCCA
          2800                                                          2850
CGATGCAGAGTTGATAGAATTGTTACAAGGGATGTATTATAGAACCAAGCCAATTAAACGGTGTATCCTTATTT
                                     2900
GGTAAGGGATAACGTATTAATAATGCCAAAGTGTTGTAACATCTTTTGTTGCGAATAAATTT
```

Fig. 8F

```
Carrot    1 ESSSKFYIAASVTTAVPSLDDSVEKVHLPRGAMWSIHKFGGTCVGSSERI  50
            :  :  |||||||:.. ||:
E.coli    1 ...............................MR.VLKFGGTSVANAERF  17
                                               * ***

51 RNVAEIVVEDDSERKL..VVVSAMSKVTDMMYDLIYKAQSRDDSYESALDA  99
            .|| ||  :  : :   .||:.|| ||  :.:|  :  :. ||
         18 LRVADILESNARQGQVATVLSAPAKITNHLVAMIEKTISGQDALPNISDA  67
                       *                     *

100 VME.KHKLTAFDLLDGD.DLARFLTRLQHDVNNLKAMLRAIYIAGHATES 147
            |||. ||:|| :  :|: .|| :| | ||  ::| ::|||: :.:.:|
         68 ERIFAELLTGLAAAQPGFPLAQLKTFVDQEFAQIKHVLHGISLLGQCPDS 117
                                                          *

148 FSDFVVGHGELWSAQLLSFVIRKNGGDCNWMDTRDVLVVNPAGSNQVDPD 197
            :: :::||||  | |||:|  |: :  :
        118 INAALICRGEKMSIAIMAGVLEARG..........HNVTVIDPVEKLLAVGH 159
                           *

198 YLESEKRLE...KWFSSNQCQT...IVATGFIASTPQNIPTTLKRDGSDF 241
            |||:   ||:. .:::::|  :   .|| || | ||||:|  .|:|| :
        160 YLESTVDIAESTRRIAASRIPADHMVLMAGFTAGNEKGELVVLGRNGSDY 209
                                       **

242 SAAIMGALLRAGQVTIWTDVNGVYSADPRKVSEAVVLKTLSYQEAWEMSY 291
            ||||: :| ||| :: :||||| |||| |:: | :| .|:||:||||: |
        210 SAAVLAACLRADCCEIWTDVNGVYTCDPRQVPDARLLKSMSYQEAMELSY 259
                * * * * **    *         *  *         * *
```

Fig. 9A

```
292 FGANVLHPRTIIPVMRYDIPIVIRNIFNLSAPGTMICRESVGETEDGLKL 341
    |-|.|||||.|:  .::|.|:|.| -  ||||:|   :..  .||::|
260 FGAKVLHPRTITPIAQFQIPCLIKNTGNPQAPGTLI...GASRDEDEL.. 304
                 *

342 ESHVKGFATIDNLALINVEGTGMAGVPGTASAIFGAVKDVGANVIMISQA 391
    .||:||:|||:|.|.:.|.|:|.|  |.|:|:.  .|:-|.-|.:|.|-.
305 ..PVKGISNLNNMAMFSVSGPGMKGMVGMAARVFAAMSRARISVVLITQS 352

392 SSEHSICFAVPESEVKAVAKALEARFRQALDAGRLSQVAIIPNCSILATV 441
    ||:|.|.|.||:..|.::|.  .|:|  .|.|:|.||:|-|:||.|:.:.|
353 SSEYSISFCVPQSDCVRAERAMLEEFYLELKEGLLEPLAVAERLAIISVV 402

442 GQKMASTPGVSATLFNALAKANINVRAIAQGCTEYNITVVLSREDCVRAL 491
    |:  .|.|-|.:|.::.-|.:|||||:|||||::|:|-|.|.|:|::: ::
403 GDGLRTLRGISAKFFAALARANINIVAIAQGSSERSISVVVNNDDATTGV 452

492 KAVHSRFYLSRTTIAVGIVGPGLIGATLLDQLRDQAAILKENSKIDLRVM 541
    :.  .::   .|.:|--.|.|:|::.|:.:|||:  |.. ||.|||||||
                                      o
453 RVTHQMLFNTDQVIEVFVIGVGVGGVGGALLEQLKRQQSWLK.NKHIDLRVC 501
                                          o

542 GITGSRTMLLSETGIDLSRWREVQKEKGQTAGLEKFVQHVRGNHFIPSTV 591
    |:::|..|:.-||:  |||:: .|||:|||.|||   ||.-|.|..:|
502 GVANSKALLTNVHGLNLENWQEELAQAKEPFNLGRLIRLVKEYHLL.NPV 550
```

Fig. 9B

```
592 IVDCTADSEVASHYHDWLCRGIHVITPNKKANSGPLDQYLKLRALQRRSY 641
    |:||..·||·:::|  |:|||||||||:.:  |— |· :|
551 IVNCTSSQAVADQYADFLREGFHVVTPNKKANTSSMDYYHQLRYAAEKSR 600
                               o  oo

642 THYFYEATVGAGLPIITTLQGLLETGDKILRIEGIFSGTLSYIFNNFKST 691
    .::.·|||||||||·|:·:·:·||—|·|—||—||·|||·:···
601 RKFLYDINVGAGLPVIENLQNLLNAGDELMKFSGILSGSLSYIFGKLDEG 650
               o              o  o       o         o

692 TPFSEVVSEAKAAGYTEPDPRDDLAGTDVARKVIILARESGLKLELSDIP 741
    ·|·... |||||||||||||·|||||—|||:::—||||—·|—·||·|||·
651 MSFSEATRLAREMGYTEPDPRDDLSGMDVARKLLILARETGRELELADIE 700
       o o  o    o           o       o      ooo 742 VQSLVPEPLRGIASAEEFLLQLPQFDSDMTRKREDAENAGEVLRYVGVVD 791
    ::·:|:·|·|·.|:·· .: —|·||·|| ·|||||| ·|—|·|·|—|·:|
701 IEPVLPAEFNAEGDVAAFMANLSQLDDLFAARVAKARDEGKVLRYVGNID 750

792 AVNQKGVVELKRYKKEHPFAQLSGSDNIIAFTTERYNKQPLIIRGPGAGA 841
    :.: ·|—·: —:||·:·:·|·|·—||·:||·  |·.|||||·|||—|||·
751 E.DGVCRVKIAEVDGNDPLFKVKNGENALAFYSHYYQPLPLVLRGYGAGN 799
           o                                     ooo 842 EVTAGGVFSDILRLASY.LGAPS* 864
    :|||||||—|·:||—|: ||
800 DVTAAGVFADLLRTLSWKLGV... 820
        oo
```

Fig. 9C

BIFUNCTIONAL PROTEIN FROM CARROTS (DAUCUS CAROTA) WITH ASPARTOKINASE AND HOMOSERINE DEHYDROGENASE ACTIVITIES

BACKGROUND OF THE INVENTION

1. Field of the Invention

The present invention relates to an isolated and purified bifunctional protein from carrots (Daucus carota L. cv Danvers) with aspartokinase and homoserine dehydrogenase activities. The invention further relates to a nucleic acid fragment encoding a bifunctional protein with aspartokinase and homoserine dehydrogenase activities.

2. Description of the Background Art

Plants can convert asparate to the amino acids methionine, threonine, lysine and isoleucine (J. Bryan, Biochemistry of Plants, (B. Miflin ed.) Academic Press, New York, pp. 403–452 (1980)). As these amino acids are essential in the diets of many animals, there is much interest in understanding the control mechanisms that determine the quantity of these essential amino acids in food sources. Enzymes control the pathways leading to the synthesis of the essential amino acids methionine, threonine, lysine and isoleucine. The isolation of clones of the enzyme genes from plants would enable one to determine the relationship between various forms of the enzymes, the number of genes involved, and the regulation of the pathway. Knowledge gained from the study of the amino acid pathway genes would allow the engineering of the pathway to alter the amino acid pool composition of plants used as protein sources.

Aspartokinase (AK.2) (E.C. 2.7.2.4) and homoserine dehydrogenase (HSDH) (E.C.1.1.1.3) catalyze steps in the pathway for the synthesis of lysine, methionine, and threonine from aspartate. AK.2 catalyzes the phosphorylation of aspartate to $\beta$-aspartyl phosphate. It is the first enzyme of the pathway leading to the synthesis of the essential amino acids lysine, threonine, methionine and isoleucine in plants. $\beta$-aspartyl phosphate is converted to aspartate semialdehyde, which can either be used to make lysine or it can be reduced by the enzyme homoserine dehydrogenase (HSDH) to homoserine. Through further enzymatic steps homoserine is converted first to phosphohomoserine and eventually to threonine and isoleucine or methionine.

In higher plants there are commonly at least two forms of AK which are differentially feedback inhibited by the end products lysine and threonine (See H. Davies et al., Plant Physiol 62: 536–541 (1978); B. Matthews et al., Planta 141: 315–321 (1978); B. Matthews et al., Z Naturforsch 346: 1177–1185 (1979); B. Matthews et al., Z Pflanzenphysiol 96: 453–463 (1980) and K. Sakano et al., Plant Physiol 61: 115–118 (1978)). HSDH.2 (EC 1.1.1.3) catalyzes the reversible conversion of aspartate semialdehyde to homoserine and is at the branch point leading to threonine, methionine and isoleucine synthesis.

Regulation of carrot (Daucus carota) AK and HSDH activities from roots and cell suspension cultures has been studied extensively (See H. Davies, supra; B. Matthews (1978, 1979, 1980) supra; J. Relton et al., Biochim Biophys Acta 953: 48–60 (1988); K. Sakano Plant Physiol 63: 583–585 (1979); and K. Sakano, supra). HSDH has been purified to apparent homogeneity and characterized (B. Matthews et al., Plant Physiol 91: 1569–1574 (1989)). Two forms of HSDH have been identified in vitro: one sensitive to threonine inhibition and one insensitive. Carrot HSDH activity reversibility converts between a threonine-insensitive form in the presence of K+ and a threonine-sensitive form in the presence of threonine which possess distinctly different electrophoretic mobilities on PAGE gels stained for enzymatic activity. Three forms of aspartate kinase have been isolated from carrot: form I is strongly inhibited by lysine, form II is strongly inhibited by threonine, and form III is partially inhibited by both. The relationship between these three forms is not yet defined. Antibody to this HSDH has been examined for specificity and cross reactivity with soybean and E. coli (F. Turano et al., Plant Physiol 92: 395–400 (1990)).

These biosynthetic pathways in plants are similar to pathways found in bacteria (G. Cohen et al., Cellular and Molecular Biology (F. Neidhardt ed.) American Society for Microbiology, Washington, D.C., pp. 429–444 (1987); and G. Cohen, Amino Acids: Biosynthesis and Genetic Regulation (K. Hermann and R. Somerville, eds.) Addison-Wesley, Reading, pp. 147–171 (1983)). Many of the bacterial genes that code for the enzymes of the aspartate pathway have been cloned and sequenced (G. Cohen (1987), supra). Only one of the plant genes in this pathway has been isolated (dihydrodipicolinate synthase (T. Kaneko, J Biol Chem 265: 17451–55 (1990)), which catalyzes the first reaction specific to lysine synthesis).

In E. coli there are three genes coding for aspartate kinase and/or homoserine dehydrogenase. One, lysC, codes for a lysine-sensitive aspartate kinass (AKIII), is regulated by lysine and does not contain HSDH activity. The other two genes code for bifunctional AK-HSDH proteins (G. Cohen (1983), supra). ThrA is repressed by threonine and isoleucine and the enzymatic activity of AKI-HSDHI is inhibited by threonine. MetL is repressed by methionine, but the protein AKII-HSDHII is not responsive to end product inhibition. It is not known if the multiple enzyme forms in plants are encoded by separate genes or if these genes are subject to transcriptional or translational regulation.

In Bacillus subtilis (R. Bondaryk et al., J Biol Chem 10: 585–591 (1985); and N. Chen et al., J Biol Chem 262: 8787–8798 (1987)), Brevibacterium lactofermentum (Mateos et al., Nucleic Acids Research 15:10598 (1987)), Rhodospirillum rubrum (P. Datta J Biol Chem 245: 5779–5787 (1970)) and Saccharomyces cerevisiae (J. Rafalski et al., J Biol Chem 263: 2146–2151 (1988)) HSDH and AK activities reside on separate proteins encoded by separate genes.

Enzymes involved in the synthesis of the aspartate family of amino acids appear to be relatively low in abundance. Homoserine dehydrogenase has been purified to homogeneity from maize (T. Walter et al., J Biol Chem 254: 1349–1355 (1979)) and carrot (B. Matthews (1989), supra), while aspartokinase has been purified to homogeneity from maize (S. Dotson et al., Plant Physiol 91: 1602–1608 (1989)) and partially purified from carrot (B. Matthews (1978, 1979), supra). There have been no indications in the literature that these two enzyme functions reside on the same protein in plants. In most of the plant species studied multiple forms of AK and HSDH have been identified in vitro (J. Bryan, supra). These forms are distinguished by their sensitivity to feedback inhibition (in particular by threonine and lysine) and by their molecular weight and subunit composition. Because there are AK activities sensitive to lysine and threonine but HSDH activity is sensitive only to threonine, a common peptide was not suspected. Although HSDH activity is associated with both lysine- and threonine-sensitive AK, the ratio of activities is variable for reasons unknown at this time. In *E. coli* AKI-HSDHI both enzymatic activities are inhibited by threonine. The *E. coli* AKIII is inhibited by lysine or threonine. Because of these *E. coli* examples, an aspartokinase sensitive to lysine and associated with threonine-sensitive homoserine dehydrogenase appears to be inconsistent.

Other factors have prevented detection of these coincident activities. It has been observed that both AK and HSDH eluted off the gel filtration column at the same location but it was assumed that it was a simple case of coelution of two large, similarly-sized proteins. The purification protocol (Matthews (1989), supra) for HSDH had already been established before the protocol for AK. In the protocol for purification of HSDH from carrot suspension culture cells (Matthews (1989), supra), a heat denaturation step is utilized and activity of AK is lost after the heat denaturation step. Even though AK activity of the *E. coli* bifunctional AKI-HSDHI is lost after heating, the comparison was not made because a bifunctional protein in plants was not suspected.

Furthermore, in contrast to *E. coli*, not all bacteria have bifunctional AK-HSDHs. In *Brevibacterium lactofermentum* separate genes encode separate AK and HSDH proteins. The *B. subtilis* gene possesses two initiation sites to produce AKI and a truncated, but functional AKII protein (N. Chen, supra). In yeast, a gene encoding AK also has been identified (J. Rafalski, supra); this gene does not appear to encode HSDH. HSDH has been extensively examined in Rhodospirillum rubrum (P. Datta et al., *J Biol Chem* 240: 3023-3033 (1965); C. Epstein et al., *Eur J Biochem* 82: 453-461 (1978); and P. Datta (1970), supra) but there are no reports in the literature that this protein also contains AK activity.

SUMMARY OF THE INVENTION

The object of the present invention is provide an isolated and purified bifunctional protein from carrots with aspartokinase and homoserine activities which can be used to regulate the amino acid content of plants, in particular the lysine, homoserine, threonine, isoleucine and/or methionine content.

It is another object of the present invention to provide a DNA molecule with a DNA sequence coding for a homologous segment of the bifunctional carrot protein.

It is a further object of the present invention to provide a method of regulating the amino acid content in a plant by bringing an effective amount of the bifunctional protein in contact with the plant.

BRIEF DESCRIPTION OF THE DRAWINGS

FIG. 8. DNA sequence of carrot AK-HSDH and the deduced amino acid sequence. Also shown are the positions of the peptides whose amino acid sequence was determined.

DETAILED DESCRIPTION OF THE PREFERRED EMBODIMENTS

Figure 1:
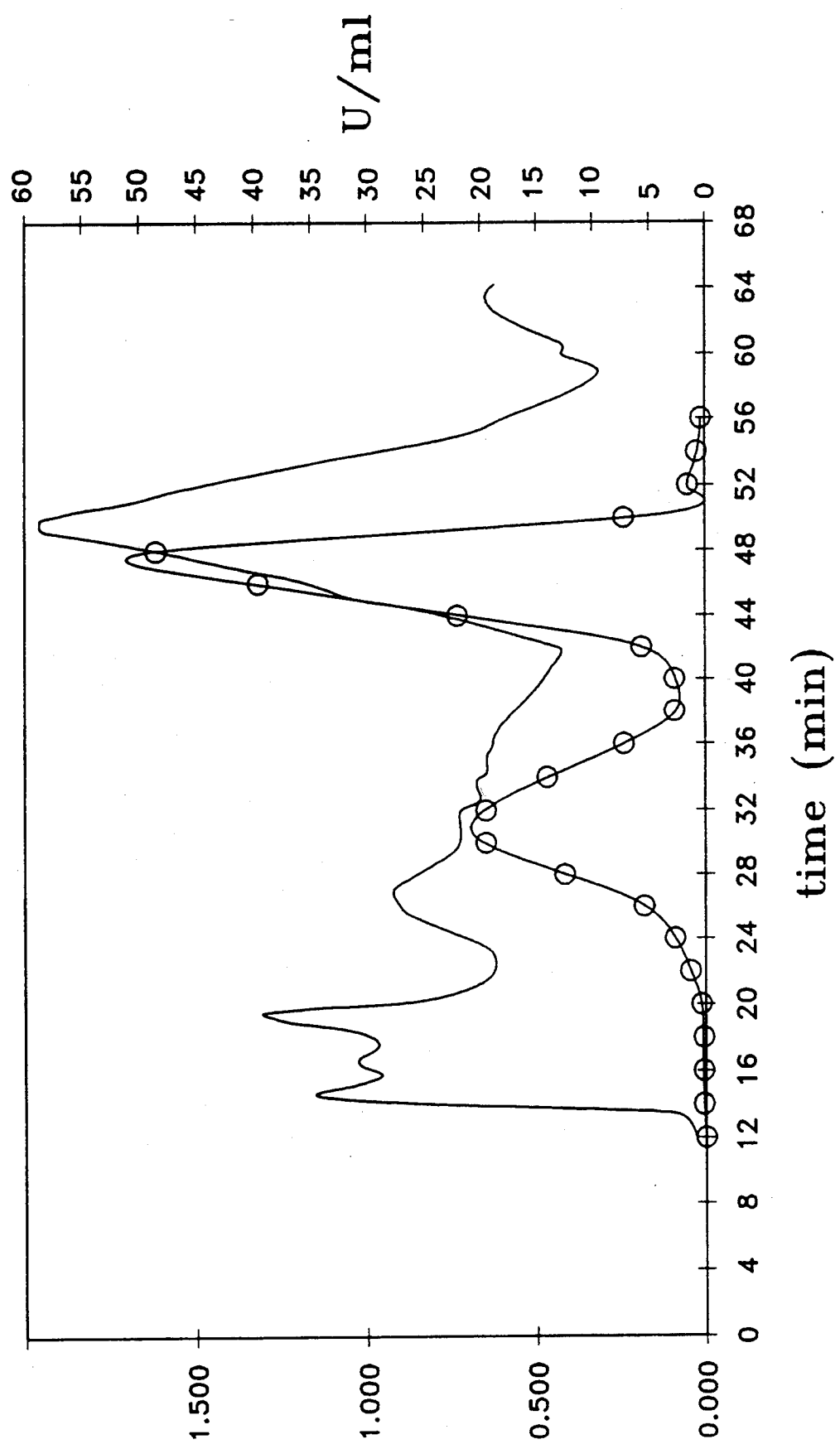
FIG. 1. Resolution of two peaks of AK activity. The AK activity (O) in U ml-1 of fractions eluted from the Altex Spherogel TSK-5PW DEAE (21.5 mm×15 cm) column equilibrated with 20 mM Mes pH 6, 5mM 2-mercaptoethanol, 1 mM lysine, 1 mM threonine and 20% glycerol is shown. The protein profile detected by a Waters Lambda-max monitor set to 280 nm is expressed as relative absorbance units.
Figure 2A:
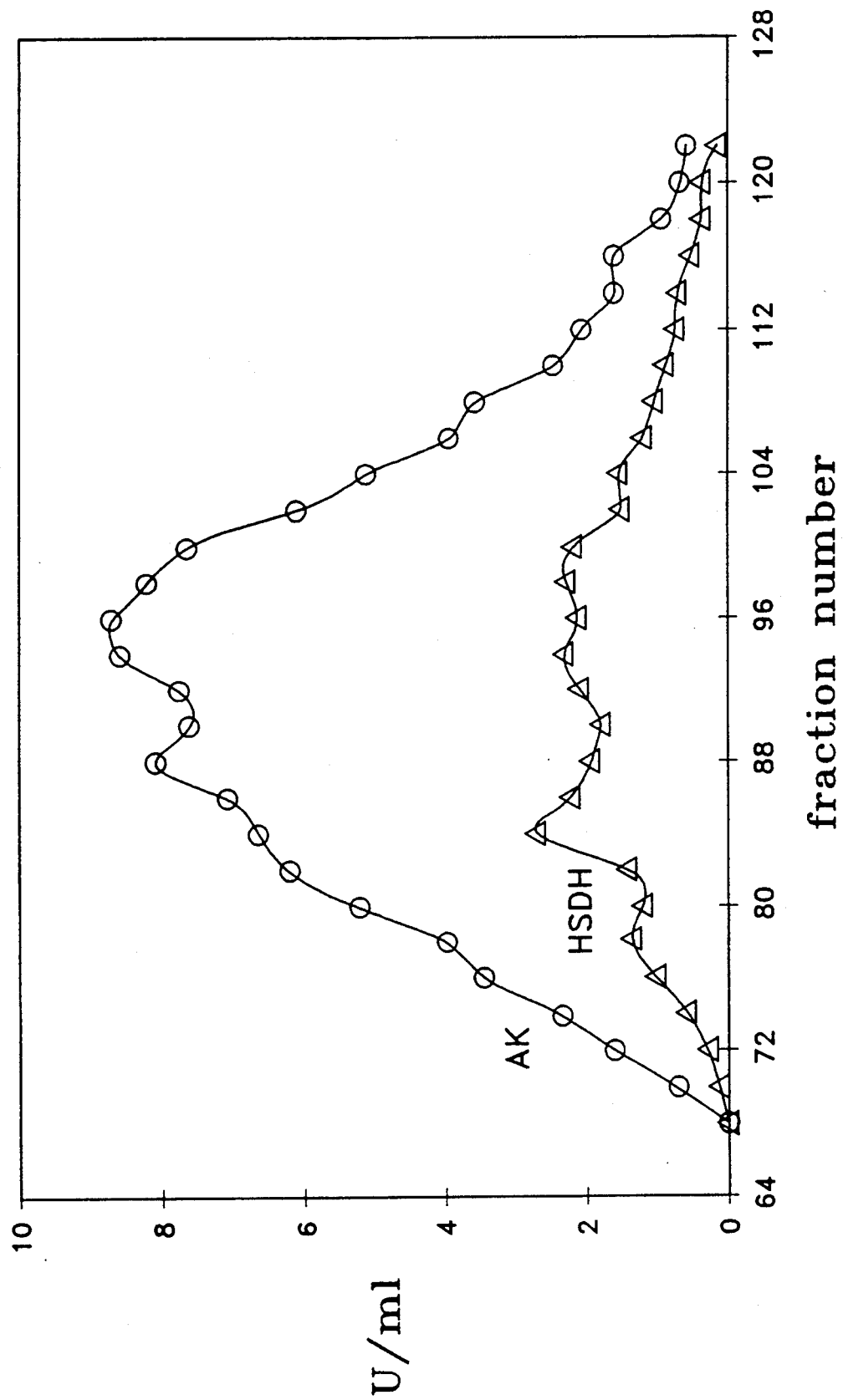
FIGS. 2A-2E. Co-elution of AK and HSDH activities. Fractions collected from gel filtration and anion exchange chromatography were assayed for AK and HSDH activities. A. Peak I activity off DEAE anion exchange at pH 7.5 with aspartate; B. Peak II activity from DEAE anion exchange at pH 6; C. Peak I activity off DEAE anion exhange at pH 7.5 with aspartate; D. Peak II activity from DEAE anion exchange at pH 6; E. Form III activity of DEAE anion exchange at pH 7.5.
Figure 2B:
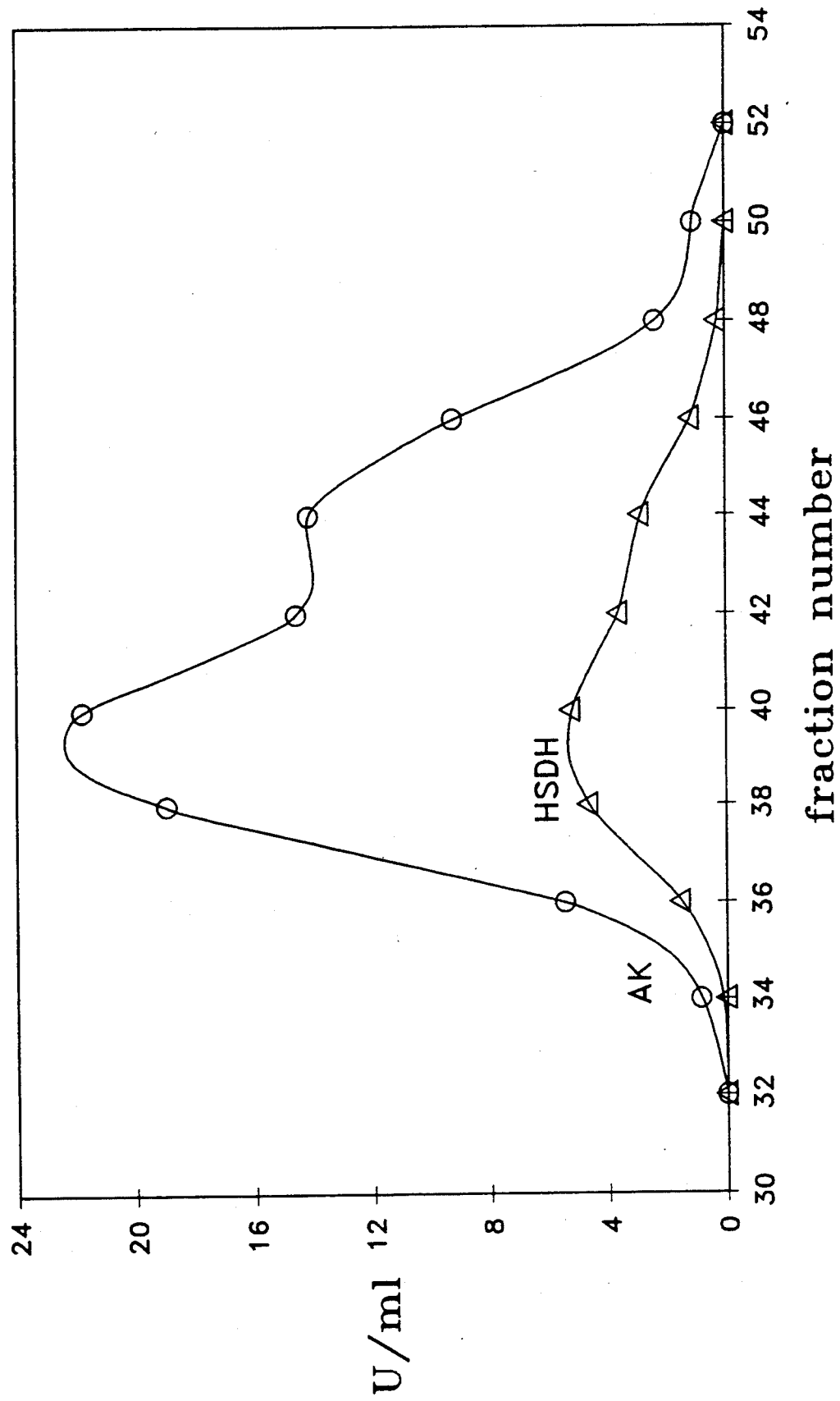
Figure 2C:
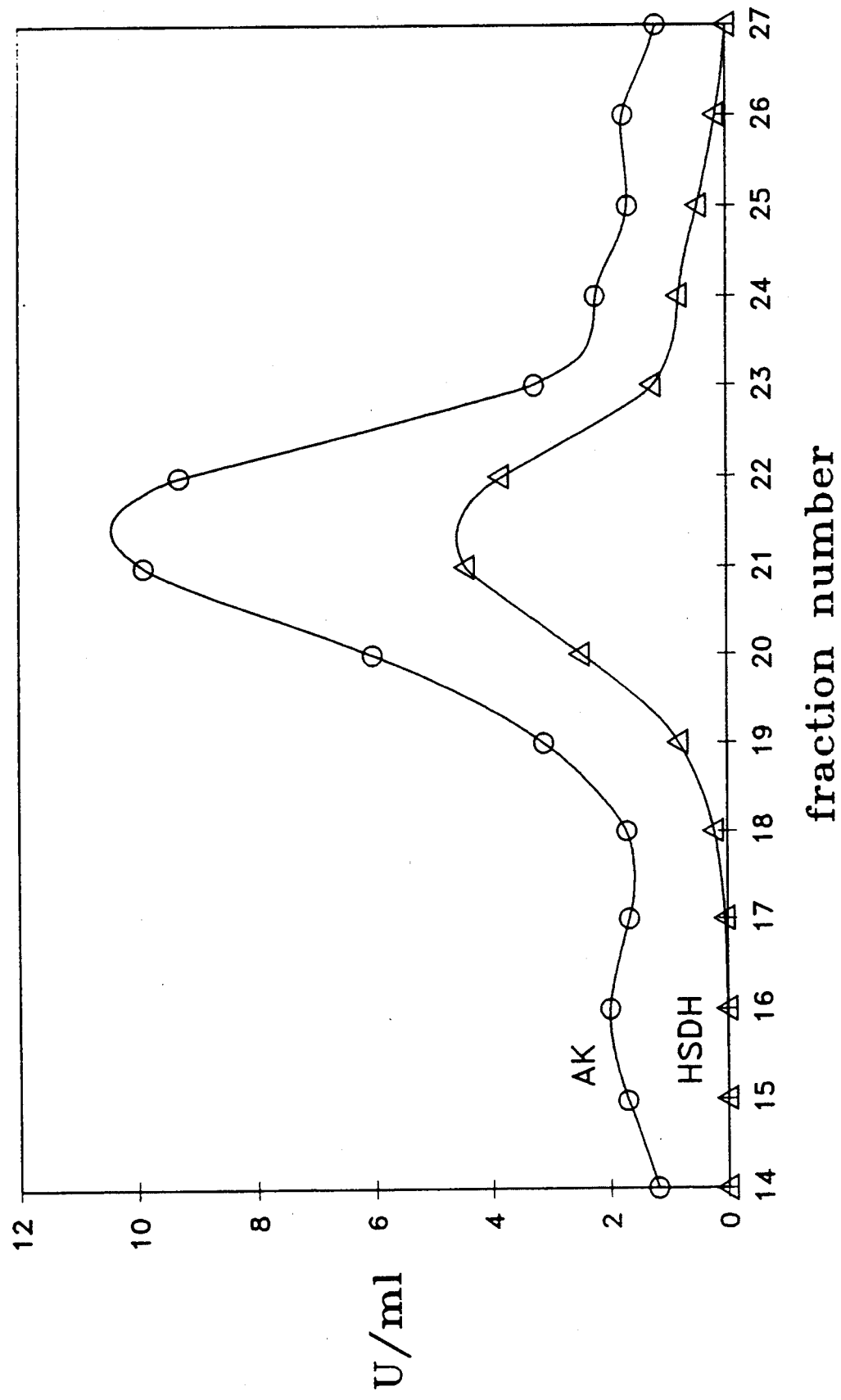
Figure 2D:
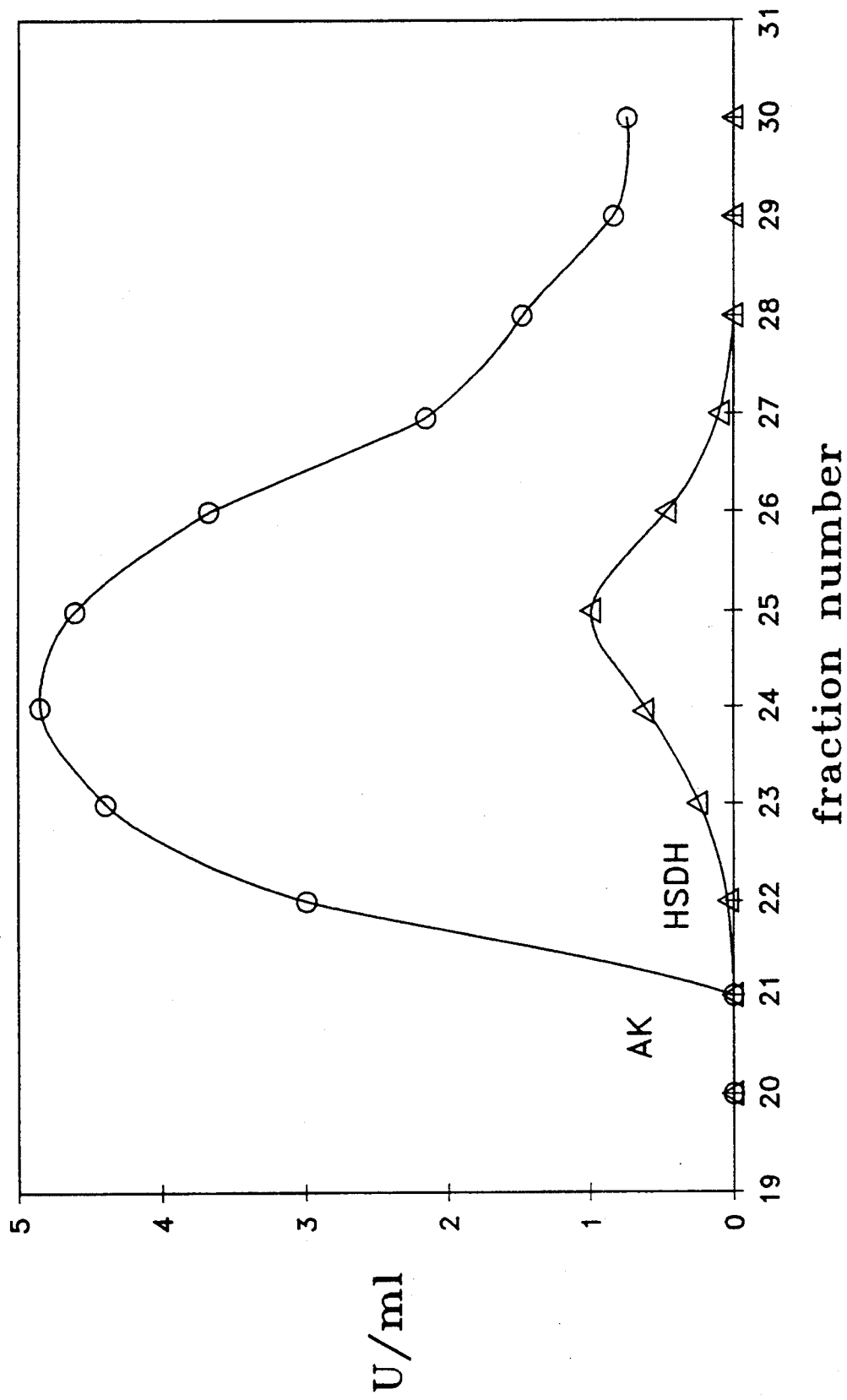
Figure 2E:
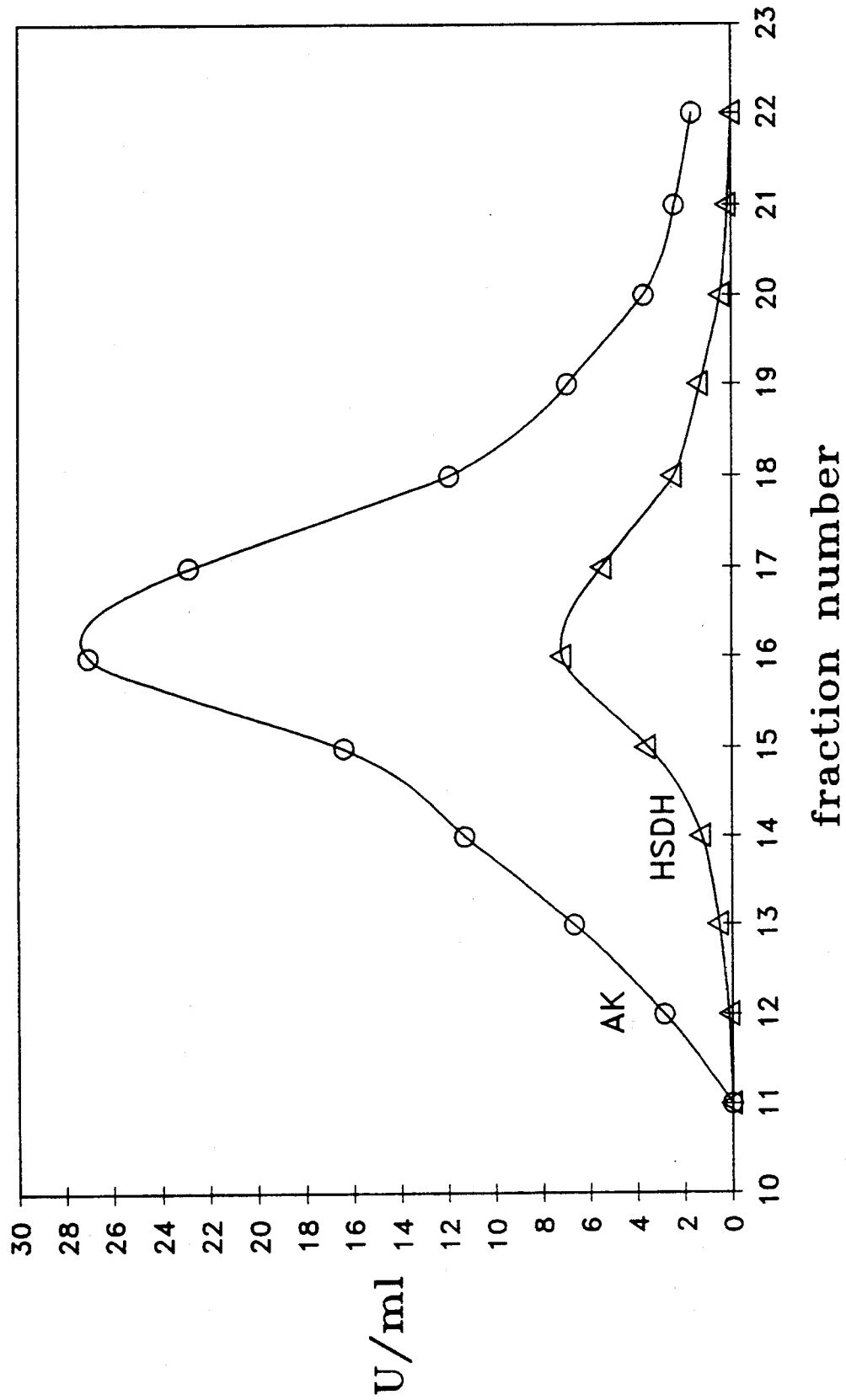

A native carrot protein has been identified to contain both aspartokinase and homoserine dehydrogenase activities and has been purified, isolated and characterized. A recombinant DNA molecule of the bifunctional enzyme has been constructed from mRNA of carrot cell suspension cultures. The activities of the enzyme are important in the biosynthesis of the nutritionally important essential amino acids lysine, threonine, methionine and isoleucine. Further, the gene and enzyme activities also may be important in synthesis of the precursor molecules of the plant hormone, ethylene.

In particular, the purified enzyme and recombinant DNA construct will be useful (1) in analyzing plant tissue to determine if they have this sequence or a similar sequence; (2) in determining the expression of the gene in the plant and specific plant tissue; (3) in making new constructs having one or the other enzyme activity; (4) in altering the recombinant DNA sequence to alter the regulation of these enzyme activities, especially to alter the amounts of the amino acid aspartate, and the nutrionally essential amino acids lysine, threonine and methionine, thus altering the nutrional value of plants, and the hormone, ethylene; (5) in identifying related sequences which also encode aspartokinase, homoserine dehydrogenase, or both; (6) in identifying their enzymes and how they are expressed; (7) in identifying DNA regulatory regions controlling the expression of this and related genes; (8) in synthesizing bulk quantities of this bifunctional plant enzyme; and (9) in gene transfer experiments as a marker.

Additionally, a DNA construct of the bifunctional enzyme gene will be useful in the field of molecular biology, particularly in the agricultural sciences. Seeds from certain crop plants are nutritionally deficient in essentail amino acids. For example, barley is low in available lysine, while soybean is low in methionine. It may be possible to improve the nutritional value of some crop plants by examining and altering the genes involved in amino acid biosynthesis, thus increasing the desired amino acid.

Homoserine dehydrogenase was purified to homogeneity and polypeptide fragments derived from digests of the protein were subjected to amino acid sequencing. Unexpectedly, the amino acid sequence of homoserine dehydrogenase from carrot indicates that both aspartokinase (AK) and homoserine dehydrogenase (HSDH) activities reside on the same protein. Additional evidence that aspartokinase and homoserine dehydrogenase reside on a bifunctional protein was provided by coelution of activities during purification steps and by enzyme specific gel staining techniques.

Highly purified fractions containing aspartokinase activity were stained for aspartokinase activity, homoserine dehydrogenase activity and protein. These gels supported the conclusion that aspartokinase activity and homoserine dehydrogenase activity were present on the same protein.

The comparison of the amino acid sequences of carrot with the other known sequences suggests that the carrot AK-HSDH is most closely related to the AKI-HSDHI of E coli because of the greater sequence homology at the AK portions of the protein. The carrot acid sequence has higher identity with the AKI-HSDHI than AKI-HSDHI has with the other E. coli fused protein AKII-HSDHII. Both carrot AK-HSDH and E. coli AKI-HSDHI are bifunctional enzymes with HSDH activities sensitive to threonine concentrations. The molecular weight of the subunit from carrot (85 kD) similar to the subunits of E. coli AKI-HSDHI (86 kD) and AKII-HSDHII (88 kD). The sequence obtained from carrot is more like the sequences from the E. coli bifunctional sequences than the other known prokaryotic HSDHs. Although different AK activities have been observed in carrot, it is not clear if these are separate gene products as in E. coli. Besides the differences in inhibition to end products, the $K_{m(asp)}$ are also different. However unlike E. coli, these different AKs in carrot may have a kinetically similar HSDH. Ligand binding is known to affect activity of the E. coli AKI-HSDHI. It has already been demonstrated that K+ or threonine binding alters the carrot HSDH. The regulation by ligand binding of a protein with two enzymatic activities can be very complex.

Protein with AK activity was partially purified by gel filtration and anion exchange chromatography. The total protein and enzymatic activity at each purification step are listed in Table I. Two peaks of AK activity were eluted from the DEAE column at pH 6.0 and identified according to their position of elution. FIG. 1 shows the resolution of two peaks of AK activity. The AK activity (O) in U ml-1 of fractions eluted from the Altex Spherogel TSK-5PW DEAE (21.5 mm×15 cm) column equilibrated with 20 mM Mes pH 6, 5mM 2-mercaptoethanol, 1 mM lysine, 1 mM threonine and 20% glycerol as shown. The protein profile detected by a Waters Lambda-max monitor set to 280 nm is expressed as relative absorbance units. DEAE is a beaded cellulose matrix crosslinked with epichlorohydrin producing diethylaminoethyl functional groups. Sephadex is a modified dextran matrix. Altex Sepherogel TSK-5PW DEAE has a base material of hydrophilic polymer derived from the Sepherogel TK 5000PW resin with the functional group DEAE (see above).

The first eluting peak (28-32 min), AKI, was inhibited by lysine and was relatively insensitive to threonine (See Table II). The second peak (44-48 min), AKII, was inhibited by threonine and was relatively insensitive to lysine. These two peaks were kinetically different as well as having different feedback inhibition patterns. The $K_{m(asp)}$ for AKI was approximately 1 mM and for AKII was approximately 9 mM. Experimental conditions could affect which AK activities were observed. AK activity inhibited by lysine was not observed unless lysine was added to the homogenization buffer. If the pH of the sample was lowered to pH 6 before anion exchange, sensitivity to lysine was lost, although the total amount of AK activity remained unchanged. If AK activity with sensitivity to both lysine and threonine were applied to cation exchange medium, activity did not bind even at pH 5 and sensitivity to lysine was lost. The amount of activity recovered in the wash was comparable to that applied. Furthermore, the lysine-sensitive activity could not be eluted from the cation-exchange medium with KCl.

TABLE I

Purification of Aspartokinase

| Sample[a] Recovery | Enzyme Units | Protein mg | Specific Activity[b] | Fold Purification | % |
|---|---|---|---|---|---|
| Crude | 1590 | 2870 | 0.55 | — | — |
| Biogel A-0.5 | 1550 | 590 | 2.6 | 4.8 | 97 |
| Sephadex G-150 | 1130 | 190 | 5.8 | 11 | 71 |
| DEAE, ph 6.0 | | | | | |
| Peak I | 180 | 10 | 17 | 30 | 11 |
| Peak II | 58 | 4.3 | 14 | 24 | 3.6 |
| DEAE, pH 7.5 | | | | | |
| Peak I | 81 | 4 | 20 | 36 | 5.1 |
| Peak II | 45 | 3 | 15 | 15 | 2.8 |
| DEAE, pH 7.5, aspartate | | | | | |
| Peak I | 4 | 0.13 | 31 | 56 | 0.25 |
| Peak II | 4 | 0.25 | 16 | 30 | 0.25 |

[a]Data from 10 preparations were averaged.
[b]Expresses as units g-1 protein.

Both forms of AK have HSDH activity associated with them, although the ratio of AK:HSDH activity was not constant (See Table II). This ratio did not correlate with the inhibition pattern of the AK form of the enzyme. Even though the AK forms were different, all had HSDH activity that was sensitive to threonine. The HSDH and AK activities co-eluted during all steps of the purification procedure. FIG. 2 shows the co-elution of AK and HSDH activities. Fractions collected from gel filtration and anion exchange chromatography were assayed for AK and HSDH activities. A. Peak I activity off DEAE anion exchange at pH 7.5 with aspartate; B. Peak II activity from DEAE anion exchange at pH 6.

No HSDH activity was detected for AK I after the anion exchange step at pH 6 but this activity could be measured after anion exchange at pH 7.5. In contrast to AKI, HSDH activity was detected with AK II after chromatography at pH 6.

TABLE II

Inhibition Pattern of AK and Ratio of Dual Activities

| Prep Number | U ml-1 AK | U ml-1 HSDH | Ratio AK/HSDH | % Control AK activity +lys (10 mM) | % Control AK activity +thr (10 mM) |
|---|---|---|---|---|---|
| ak32I | 22 | 360 | 0.06 | 21 | 68 |
| ak33I | 8 | 2200 | 0.004 | 39 | 71 |
| ak33II | 8 | 5600 | 0.002 | 75 | 32 |
| ak45II | 48 | 3200 | 0.02 | 91 | 33 |

In addition to the co-purification of AK and HSDH activities, the activities co-migrated on native PAGE. All three forms of AK had a bank of AK activity migrating to the same location on native PAGE. Frequently, forms I and III had an additional faster-migrating band of AK activity appearing on gels but HSDH activity appeared consistently with the slower-migrating band.

Figure 3:
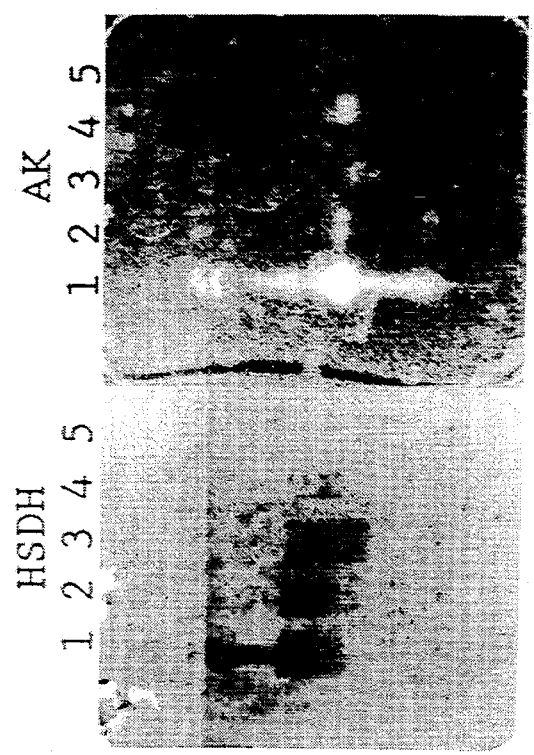
FIG. 3. AK and HSDH activity stains on polyacrylamide gels. Samples (4 ul) of forms I and II were loaded onto 8-25% polyacrylamide gel. The gel was first stained for AK activity and photographed (A) and then stained for HSDH activity and photographed (B). Lane 1: ak44 with 1.2 U of AK (Form II) and 127 U of HSDH; Lane 2: ak41 with 0.08 U of AK (mix of Forms I and II) and 7 U of HSDH; Lane 3: akxx (mixture) with 0.1 U of AK (Form II) and 7 U of HSDH; Lane 4: ak32 with 0.09 U of AK (Form I) and 1 of HSDH; Lane 5. ak31 with 0.09 U of AK (mix of Forms I and II) and 5.4 U of HSDH.

FIG. 3 shows the AK and HSDH activity stains on polyacrylamide gels. Samples (4 ul) of forms I and II were loaded onto 8–25% polyacrylamide gel. The gel was first stained for AK activity and photographed (A) and then stained for HSDH activity and photographed (B). Lane 1: ak44 with 1.2 U of AK (Form II) and 127 U of HSDH; Lane 2: ak41 with 0.08 U of AK (mix of Forms I and II) and 7 U of HSDH; Lane 3: akxx with 0.1 U of AK (Form II) and 7 U of HSDH; Lane 4: ak32 with 0.09 U of AK (Form I) and 1 of HSDH; Lane 5. ak31 with 0.09 U of AK (mix of Forms I and II) and 5.4 U of HSDH.

With Form II there was usually only one band of AK activity but the HSDH activity appeared as a ladder extending above the AK band (FIG. 3). This ladder has been described as aggregates of HSDH (Mattews (1989), supra). Lack of AK activity appearing with the HSDH activity ladder was thought to be due to the lack of sensitivity of the AK activity stain on gels. A very active sample of AK (AK44II) which has about ten times the activity of most AK samples gives a ladder of AK as well as HSDH activity on a gel (FIG. 3).

The cross reactivity with forms of AK by antibody made to purified carrot HSDH (Turano, Supra) was investigated. Equal amounts of protein of each AK form were subjected to PAGE. Half of the gel was stained for HSDH activity and the other half was electroblotted onto nitrocellulose. Form I had about half the HSDH activity of form II and the sample that was a mixture of forms I and II; all had different AK activity. The nitrocellulose blot was incubated with antibody specific to carrot HSDH (Turano, supra). Antibody bound to all three samples of AK (FIG. 4) indicating immunological similarity amongst the forms.

Figure 4:
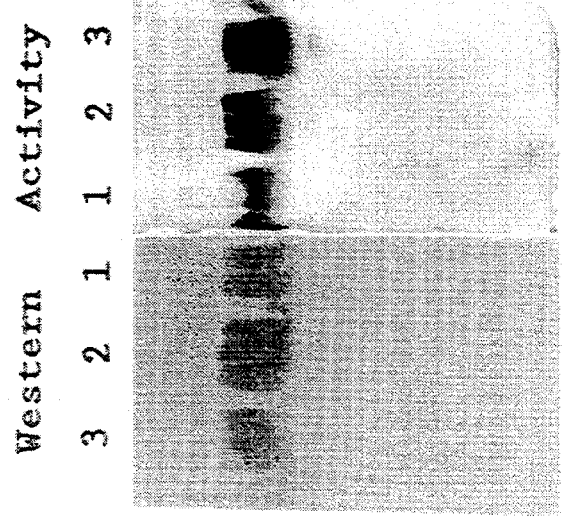
FIG. 4. Western blot of samples of AK with antibody against HSDH. Equal amounts of protein (4 ug) of samples of AK I, II and III were loaded onto 10-15% polyacrylamide gels. Half of the gel is electroblotted onto nitrocellulose for incubation with antibody and half is stained for HSDH activity. Lane 1: ak6 (Form I) with 6 U HSDH; Land 2: ak33 (Form II) with 22 U HSDH; Lane 3: ak20 (mix of Forms I and II) with 15 U HSDH.

FIG. 4 shows the Western blot of samples of AK with antibody against HSDH. Equal amounts of protein (4 ug) of samples of AK I, II and III were loaded onto 10–15% polyacrylamide gels. Half of the gel is electroblotted onto nitrocellulose for incubation with antibody and half is stained for HSDH activity. Lane 1: ak6 (Form I) with 6 U HSDH; Land 2: ak33 (Form II) with 22 U HSDH; Lane 3: ak20 (mix of Forms I and II) with 15 U HSDH.

Further evidence that the two enzymatic activities reside on the same polypeptide is provided by amino acid sequence data. Two peptide fragments derived from purified HSDH were sequenced. A sequence of 29 amino acids were obtained from peptide 97 (See Table III). This sequence had some identity with portions of known HSDH genes from prokaryotes (Matthews (1989), supra), especially with the HSDH regions of the two E. coli HSDHs (Table III). Carrot HSDH possessed 48% identity with the corresponding section of both AKI-HSDHI (ThrA) and 52% identity with AKII-HSDHII (MetL). The carrot HSDH possessed only 38% amino acid identity with HSDH from *Bacillus subtilis* and 34% identity with *Brevibacterium lactofermentum*.

TABLE III

| | Sequence Identity of Peptide 97 | | |
|---|---|---|---|
| Source | Amino Acid Sequence | % Identity | Ref |
| carrot | SYTHY FY—EAT VGAGL PIITT LQGLL ETGD | | |

TABLE III-continued

Sequence Identity of Peptide 97

| Source | Amino Acid Sequence | % Identity | Ref |
|---|---|---|---|
| thrA (AKI-HSDHI) | (SEQ ID NO: 1)<br>SRRKF LK-DIN VGAGL PVIEN LQNLL NAGD | 48 | 11 |
| metL (AKII-HSDHII) | (SEQ ID NO: 2)<br>TGRHW LY—NAT VGAGL PINHT VRDLI DSGD | 52 | 24 |
| B. subtilis | (SEQ ID NO: 3)<br>ENGCD TYFEAS VAGGI PILRT LEEGL SS—D | 38 | 4 |
| B. lactofermentum | (SEQ ID NO: 4)<br>—N—VD LYFEAA VAGAL PVVCP LRRSL —AGD | 34 | 12 |
| | (SEQ ID NO: 5) | | |

A sequence of 21 amino acids was obtained from peptide 76. This sequence corresponded to a portion of the amino acid sequence of several known aspartokinases (See Table IV) from prokaryotes and yeast (M. Cassan et al., J Biol Chem 261: 1052-1057 (1986); M. Katinka et al., Proc Natl Acad Sci, USA 77: 5730-5733 (1980); M. Zakin et al., J Biol Chem 258: 3029-3031 (1983);N. Chen, supra, J. Rafalski, supra). The amino acid identity between the carrot AK and the corresponding AKregion of AKI-HSDHI (ThrA) of E. coli was 76% and identity was both AKIII(LysC) of E. coli and AK from B. subtilis was 52%. The identity with AKH-HSDHH (MetL) was 43% and was only 38% with yeast AK.

TABLE IV

Sequence Identity of Peptide 76

| Source | Amino Acid Sequence | % Identity | Ref |
|---|---|---|---|
| carrot | TLDYQ EAWEM SYFGA NVLHP R<br>(SEQ ID NO: 6) | | |
| thrA (AKI-HSDHI) | SMSYQ EAMEL SYFGA KVLHP R<br>(SEQ ID NO: 7) | 76 | 11 |
| MetL (AKII-HSDHII) | LLRLD EASEL ARLAA PVLHA R<br>(SEQ ID NO: 8) | 43 | 24 |
| LysC (AKIII) | EIAFA EAAFM ATFGA KVLHP A<br>(SEQ ID NO: 9) | 52 | 3 |
| B. subtilis | GISYD EMLEL ANLGA GVLHP R<br>(SEQ ID NO: 10) | 52 | 4 |
| yeast | SVTPE EASEL TYYGS EVIHP F<br>(SEQ ID NO: 11) | 38 | 18 |

When the amino acid identities of the two sequences from carrot were compared to other known AK and HSDH sequences, carrot was found to be more closely related to the E. coli bifunctional AKI-HSDHI than to E. coli AKII-HSDHII or to the B. subtilis AK and HSDH which are separate proteins. The identity of the carrot AK-HSDH with E. coli AKI-HSDHI was greater than the identity between any other two sequences; for example, the identity between E. coli AKI-HSDHI and E. coli AKII-HSDHII was only 34% for peptide. The locations of the sequenced peptides from carrot have been identified on the AKI-HSDHI and are shown in FIG. 5.

Figure 5:
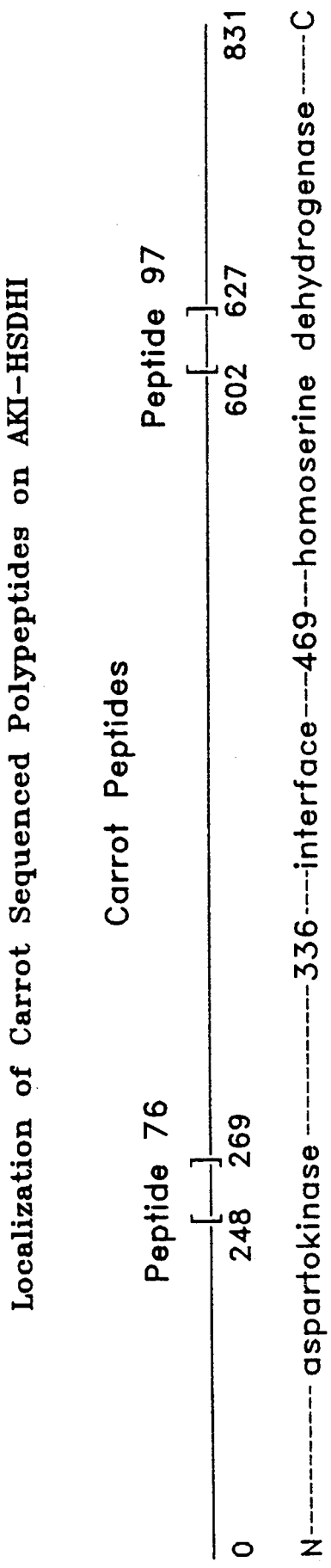
FIG. 5. Localization of carrot sequenced polypeptides on *E. coli* AKI-HSDHI. The peptide sequences from FIGS. 3 and 4 are indicated on the homologous region of *E. coli* AKI-HSDHI. The regions of the *E. coli* protein with AK and HSDH activities are shown on either side of an interface region.

In FIG. 5, localization of carrot sequenced polypeptides on E. coli AKI-HSDHI is shown. The peptide sequences from FIGS. 3 and 4 are indicated on the homologous region of E. coli AKI-HSDHI. The regions of the E. coli protein with AKand HSDH activities are shown on either side of an interface region.

Oligonucleotides based on amino acid sequences from the purified protein were used to amplify a DNA fragment from carrot cell culture RNA. The amplification product was used to probe cDNA libraries from carrot cell culture and root RNA. Two overlapping clones were isolated. Together the complete cDNA clone is 2915bp long and has a single long open reading frame for 864 amino acids. The isolated carrot cDNA encodes a bifunctional aspartokinase-homoserine dehydrogenase enzyme.

Previous studies of plant enzymes gave no evidence of the existence of a bifunctional AK-HSDH in plants. Such forms had not been found outside of the Enterobacteriaceae. The DNA sequence of the isolated carrot cDNA, as well as further analysis of the carrot enzyme, unexpectedly reveal that carrot has a bifunctional AK-HSDH similar to that found in E. coli. The most common situation is the existence of separate aspartokinase and homoserine dehydrogenase proteins. Since the carrot cDNA is the first aspartokinase or homoserine dehydrogease clone isolated from a plant, it is not known if such fused genes are common in plants. However, a partial clone isolated from soybean has approximately 80% identity to the carrot clone and appears to also encode both AK and HSDH.

Although the cDNA clone has a potential start site for translation, it is doubtful that this is the actual start. HSDH and AK have been shown to be localized in the chloroplasts of several plant species (J. Bryan et al., Plant Physiol 59: 673-679 (1977); P. Lea et al., FEBS Lett 98: 165-168 (1979); W. Mills et al., Planta 142: 153-160 (1978); J. Sainis et al., Planta 152: 491-496 (1981); and R. Wallsgrove et al., Plant Physiol 71: 780-784 (1983)) and are probably localized in the chloroplast of carrot. It follows that the carrot AK-HSDH probably has a chloroplast transit peptide at the amino terminus, since all known proteins transported into the chloroplast have transit peptides (K. Keegstra et al., Annu Rev of Plant Physiol and Plant Mol Biol 40: 471-501 (1989)). The reading frame of the clone is continuous from the second base pair through the conserved KFGGT sequence which is found near the amino-terminus of all AK proteins. The 30-35 amino acids encoded by the 5' end of the clone have the character of chloroplast transit peptides: the string is rich in serine, threonine, and small hydrophobic amino acids (K. Keegstra, supra). The sequence of the amino-terminus of the purified HSDH could not be determined and no precursor with a transit peptide has been identified.

Availability of the AK-HSDH bifunctional enzymes in mass quantity provides the opportunity to introduce regulation and control of plant conversion of aspartate to the amino acids methioninem threonine, lysine and isoleucine. Either by directly applying the enzyme to plants or by inserting the controlling genes into seeds, one can alter the amino acid concentration in food sources. Since availability of quantities of the enzymes is a major limiting factor in the commercial use of the isolated and purified enzymes, reliable sources must be secured prior to field trials and large scale test implementation. Using conventional biotechnology techniques, such sources can be secured.

Using conventional techniques such as dideoxy chain termination method of Sanger et al., supra, the DNA sequence can be determined for the proteins which encode the amino acid sequence of the homologous segement of the purified and isolated bifunctional enzyme. The phrase "homologous segment of the enzyme" means an amino acid sequence sufficiently duplicative of the protein of the present invention to allow the possession of the unique properties of the isolated and purified bifunctional enzyme.

Two DNA sequences are "substantially homologous" when at least 77 to 90%, preferably 80 to 90% and most preferably 85%, of the nucleotides match over the defined length of the selected region that encodes for the enzyme. Defining appropriate hybridization conditions is within the skill of the art.

On the basis of the genetic code, there exits a finite set of nucleotide sequences which can genetically code for a given amino acid sequence. All such equivalent nucleotide sequences are operable variants of the disclosed sequence, since all give rise to the same protein, having the same amino acid sequence, during the course of an in vivo transcription and translation. Consequently, all such variants are intended to be included in the scope of the present invention.

A cDNA expression library was constructed in the bacteriophage vector lambda-gt11 using poly A mRNA purified from carrot cell culture and carrot root. The cDNA library was screened with using radiolabelled PCR product as a probe. The coding sequence can be contained in vectors which are operable as cloning vectors or expression vectors when inserted into an appropriate host. The expression vector may be for example a replicon, plasmid, bacteriophage, virus or hybrid thereof. The vectors used in practicing the invention are selected to be operable as cloning vectors or expression vectors in the selected host cell. Numerous cloning vectors known to those skilled in the art, and selection of an appropriate cloning vector is a matter of choice. Examples of cloning vectors include the bacteriophage lambda-gt11, M13mp18 amd mp19. See generally Maniatis et al., DNA Cloning: A Practical Approach, Volumes I and II (D. Glover, ed.) IRL Press, Oxford (1985); and J. Sambrook et al., Molecular Cloning: A Laboratory Manual, 2nd Edition, Cold Spring Harbor Press, Cold Spring Harbor, N.Y. (1989).

The encoding DNA or expression vector of the present invention can be expressed in mammalian cells or other eukaryotic cells, such as yeast, or in prokaryotic cells, in particular bacteria. Bacterial strains may be utilized as hosts for the production of the enzymes of the present invention, such as E. coli strains and other enterobacteria such as Salmonella, Serratia and Pseudomonas.

The deduced amino acid sequence of the carrot HSDH shows homology to bacterial aspartokinases and homoserine dehydrognases and to yeast aspartokinase. The most striking homology is to the E. coli AKI-HSDHI protein. The overall homology between the carrot HSDH and E. coli AK-HSDH (48%) is higher than that between the two E. coli AK-HSDH proteins (39%) (M. Zakin, supra). It has been proposed that AKI-HSDHI consists of three domains: an amino-terminal domain with aspartokinase activity (amino acids 1 to approximately 249), a carboxy-terminal domain with homoserine dehydrogenase activity (amino acids 471 through 820), and an interface domain (amino acids 250–470) (J. Rafalski, supra). The regions of the carrot protein that are most similar to AKI-HSDHI are the interface and homoserine dehydrogenase domains. In contrast the homology between the carrot protein and E. coli AKII-HSDHII is lowest in the interface region. The homology in the other regions is only slightly lower for AKII-HSDHII than for AKI-HSDHI. Both the carrot enzyme and AKI-HSDHI are regulated by threonine, whereas AKII-HSDHII is not. The higher homology between the two proteins may be related to this regulation.

In order to understand the regulation of these genes and the enzyme activities one needs tO know the number of genes and the number of distinct forms of the enzymes that exist. It has not been determined if the isolated cDNA represents the only AK or HSDH gene in carrot. Studies on the HSDH enzyme of carrot indicate that there is only one HSDH protein, but this protein has different subunit structure and different regulatory properties depending on solution conditions (Matthews ((1989), supra). Studies on the AK function have shown three forms of enzyme which differ in their sensitivity to lysine and threonine. Some of these forms appear to interconvert. There is no conclusive evidence yet as to whether all the forms of carrot AK and HSDH are separate proteins or if they are forms of the same protein. There is also no definitive proof that the cDNA clone described here represents the only carrot gene for AK and HSDH. DNA blots probed with the carrot cDNA indicated a low number of hybridizing sequences in the genome, and RNA blots showed predominantly one band of about 3000 nucleotides. However, genes with only slight variations may not have been seen as different in these experiments and genes with low homology might not be uncovered at all. In contrast to the carrot results, experiments with a soybean clone show a much more complex pattern of DNA and RNA hybridization4. It is possible that carrot has only the one AK-HSDH which has both enzymatic functions and is regulated both by threonine and lysine.

Having now generally described the invention, the same will be further understood by reference to certain specific examples which are included herein for purposes of illustration only and are not intended to be limiting.

EXAMPLE I

Plant Material and Enzyme Extraction

Cell suspension cultures of carrot (Daucus carota L. cv Danvers) were grown in flasks containing 200 ml of defined liquid medium as described in B. Mattews (1978), supra. HSDH activity was purified to homogeneity as described in B. Matthews (1989), supra. The proteins from polyacrylamide electrophoretic gels containing HSDH were blotted onto nitrocellulose paper and analysed for their amino acid sequencing. Sequence data was obtained from peptides separated by reverse-phase chromatography of digests of HSDH with trypsin, after it was determined that the N-terminal amino acid was blocked.

AK was purified by a series of column chromatography steps. The cells were harvested after 5 days and disrupted in a nitrogen bomb as described for HSDH (B. Matthews (1989), supra) except that the threonine concentration was reduced to 1 mM and 1 mM lysine was added to the extraction buffer. The crude extract was concentrated by 60% ammonium sulfate before the first gel filtration through Biogel A-0.5 m (4.5 cm×47 cm) equilibrated with 50 mM Tris-HCl pH 7.5, 10 mM 2-mercaptoethanol, 1 mM EDTA, 1 mM lysine, 1 mM threonine and 20% glycerol. Fractions containing AK activity were combined, concentrated by the addition of an equal volume of saturated ammonium sulfate for a second gel filtration through Sephadex G-150 (2.5 cm×39 cm) and equilibrated with the same buffer plus 0.2 M KCl. Fractions with AK activity were combined, concentrated by the addition of an equal volume of saturated ammonium sulfate and dialyzed against 16 mM Tris-HCl pH 7.5, 10 mM 2-mercaptoethanol, 1 mM lysine, 1 mM threonine and 20% glycerol. The dialyzed sample was loaded onto an Altex Spherogel TSK DEAE-5PW column (21.5 mm×15 cm). AK activity was eluted over 65 min with a gradient from 0–0.5 M KCl in 20 mM Mes pH 6, 5 mM 2-mercaptoethanol, 1 mM lysine, 1 mM threonine, and 20% glycerol. Fractions containing activity were combined, diluted four-fold and applied to an Altex Spherogel TSK DEAE-5PW column (7.5 mm×7.5 cm) equilibrated with 50 mM Tris-HCl pH 7.5 containing 5 mM 2-mercaptoethanol, 1 mM lysine, 1 mM threonine and 20% glycerol fractions containing AK activity were combined and diluted four-fold and reapplied to the column equilibrated with the same buffer containing 20 mM aspartate. Fractions with AK activity were concentrated by filtration through Centricon-303 filters (Amicon) and stored at $-20°$ C.

EXAMPLE II

Enzyme and protein assays and stains

Aspartokinase activity was assayed by the hydroxamate method as described in P. Bryan et al., *Biochem Biophys Res Comm* 41: 1211–1217 (1970). The assay mixtures contained 100 mM Tris, pH 8.0, 50 mM hydroxamate-KOH, 50 mM L-aspartate, 40 mM ATP, and 20 mM Mg2SO4 and were incubated at 37° C. for 60 min. The reaction was terminated by the addition of a solution of 0.37 M FeCl3, 0.20 M trichloroacetic aid and 0.72 M HCl. One unit (U) of activity produced 1 umol β-aspartylphosphate $hr^{-1}$. Zero time controls were included. Activity was visualized on polyacrylamide gels (Phast System by Pharmacia, Upsala, Sweden) by incubating gel slices at 37° C. in 50 mM Tris-HCl pH 7.5, 50 mM aspartate 10 mM ATP, 50 mM MgSO4, 1 mM DTT, 20% glycerol, 0.014 gm $ml^{-1}$ 0.02% Alizarin red S (H. Nimmo et al., *Anal Biochem* 121: 17–22 (1982); and J. Relton, supra). To show specific aspartate kinase activity, duplicate gel strips were incubated without aspartate and also in aspartate with 10 mM lysine and/or 10 mM threonine.

HSDH activity was assayed in the direction of coenzyme reduction as described in B. Matthews (1989), supra. Enzyme preparations were analyzed on 8–15% gradient polyacrylamide gels using a Phast (Pharmacia, Upsala, Sweden) gel electrophoresis system. HSDH activity was located on the gel as described in B. Mattews (1978), supra, using 60 mM Tris-HCl (pH 9.0), 150 mM KCl, 30 mM AND+, 24 mM homoserine, 0.22 mM 2-mercaptoethanol, 0.15 mM EDTA, 0.266 mg $ml^{-1}$ nitro blue tetrazolium and 0.025 mg $ml^{-1}$ phenazine methosulfate incubated at 37° C. Gels incubated in the staining mixture lacking homoserine were used as controls.

Protein was visualized on gels using silver nitrate according to the manufacturer's instructions (Pharmacia).

EXAMPLE III

Western Blot Analysis

The backing of the Phast gel was removed using a razor blade. The protein in the polyacrylamide gel was then electroblotted onto nitrocellulose in 25 mM Tris, 20 mM glycine, pH 8.3 at 25–35 V for 1 hour at 4° C. Excess protein binding sites were blocked by incubating the filters in 1×TBS2, 1.0% dry milk and 0.5% BSA for a hour at room temperature. Nitrocellulose filters were incubated with primary antibody (anti-HSDH antiserum from mouse), secondary and tertiary antibody and the alkaline phosphatase activity visualized as described by F. Turano, supra.

EXAMPLE IV

General DNA Cloning Methods

Plasmid DNA preparation, ligations, restriction enzyme digestions, Southern blots, Northern blots were done according to standard procedures (T. Maniatis et al., *Molecular Cloning: A Laboratory Manual,* Cold Spring Harbor Laboratory, Cold Spring Harbor, N.Y. (1982)). Plant genomic DNA was extracted by the method of P. Keim et al., Soybean Genetics Newsletter 15:150–152 (1988). Enzymes were obtained from either Bethesda Research Laboratories or Boehringer Mannehim. PCR reagents were from Perkin-Elmer Cetus. Oligonucleotides used for PCR were obtained from Synthecell.

DNA probes were labelled with [α-$^{32}$P] dCTP (DuPont-New England Nuclear) using the random oligonucleotide priming method described by A. Feinberg, *Anal Biochem* 132: 6–13 (1983).

DNA sequence determination was done by the dideoxy chain termination method using modified T7 DNA polymerase (Sequenase 2.0 from United States Biochemical Corp.) (F. Sanger et al., *Proc. Natl. Acad. Sci. U.S.A.* 74: 5463–5467 (1977)).

EXAMPLE V

Construction of a Carrot cDNA Library

Total RNA was extracted from two-month old carrot roots using the method described by J. Chirgwin et al., *Biochem* 18: 5294–5299 (1979). Poly (A)+ RNA was isolated from total RNA on columns of oligo (dT) cellulose (Maniatis, supra). cDNA was made from 3 ug poly (A)+ RNA using the cDNA Synthesis System Plus from Amersham. EcoRI adaptors were added (Promega "Riboclone EcoRI Adaptor Ligation System") and the cDNA was ligated with lambda-gt11 arms (Promega) and packaged using Stratagene "Gigapack II Plus" packaging extracts. The phage were plated and screened following methods described by Maniatis, supra. Approximately 240,000 plaques were screened using a radiolabelled PCR product as the probe. Lifts were done in duplicate onto nitrocellulose filters. Filters were hybridized in 50% formamide/5×-Denhardt's solution/5×SSPE/0.1% SDS/100 ug/ml denatured salmon sperm DNA at 42° C. for 18 hr. The final wash was with 0.1×SS/0.1% SDS at 45° C. for one set of filters and 60° C. for the second set.

A second cDNA library was constructed in the same manner, except that poly (A)+ RNA from carrot cell culture was used and first strand synthesis was primed with an oligonucleotide corresponding to a tryptic peptide from purified carrot HSDH (HSDH97: 5'-GCT/CTCA/GTAA/GAAA/GTAA/GTGN-GTA/GTA). (SEQ ID NO: 12)

EXAMPLE VI

PCR Amplification of Carrot cDNA Encoding HSDH

HSDH protein purified from carrot cell suspension cultures was subjected to proteolysis and the polypeptides were separated by high pressure liquid chromatography (HPLC). The amino acid sequences of four polypeptides were determined. Based on the amino acid sequence of two of these polypeptides two oligonucleotides were synthesized:

Oligo HSDH 76: 5'-TAT/C CAA/G GAA/G GCN TGG GAA/G ATG (SEQ ID NO: 13) (Peptide 76: NH2-YQEAWEM) (SEQ ID NO: 14)

Oligo HSDH 97: 5-GCT/CTC A/GTA A/GAA A/GTA A/GTG NGT A/GTA (SEQ ID NO: 12) (Peptide 97: A E Y F Y H T Y-NH2) (SEQ ID NO: 15)

These oligonucleotides were used as primers for PCR amplification of carrot cDNA. Both double-stranded cDNA made from carrot root poly(A)+ RNA and a first-strand cDNA made from carrot cell culture poly(A)+ RNA served as templates. When the amplification was carried out at an annealing temperature of 52° C., using either template, predominantly an 1100bp product was obtained.

Figure 6:
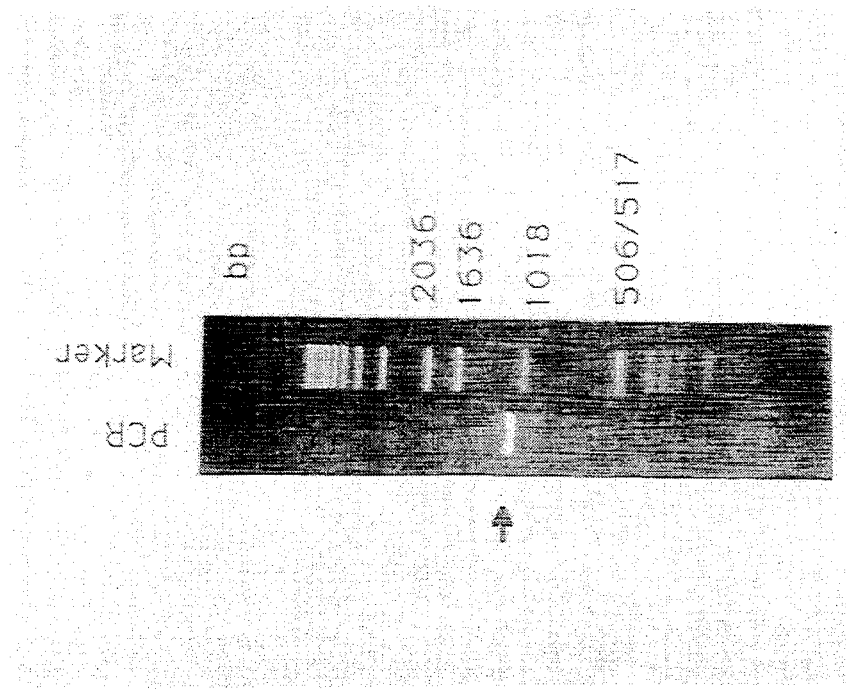
FIG. 6. Product of PCR amplification of a carrot cDNA segment encoding HSDH. Poly (A)+ RNA from carrot cell suspension cultures was used for first-strand cDNA synthesis. This cDNA was used as the template for PCR amplification with primers HSDH 76 and HSDH 9. Amplification was carried out at an annealing temperature of 52° C. for 30 cycles.

FIG. 6 shows the product of PCR amplification of a carrot cDNA segment encoding HSDH. Poly (A)+ RNA from carrot cell suspension cultures was used for first-strand cDNA synthesis. This cDNA was used as the template for PCR amplification with primers HSDH 76 and HSDH 9. Amplification was carried out at an annealing temperature of 52° C. for 30 cycles.

The PCR product was analyzed by restriction endonuclease digestion. A 579bp EcoRI-HindIII fragment was subcloned into vectors M13mp18 and mp19 and the DNA sequence was determined.

EXAMPLE VII

Isolation of Lambda-gt11 Carrot cDNA Clones for HSDH

The 1100bp PCR amplified DNA fragment was used to screen a carrot cDNA library. The library was constructed in the vector lambda-gt11 and contained cDNA from carrot root poly(A)+ RNA. From approximately 250,000 plaques four clones were obtained. All of the clones displayed similar restriction digestion patterns and appeared to differ from one another only in length.

The complete DNA sequence of the longest clone, HSDH1, was determined. The clone was 2079bp long and had one long open reading frame starting at base 1 and reading through base 1755 for a total of 585 codons.

Figure 7:
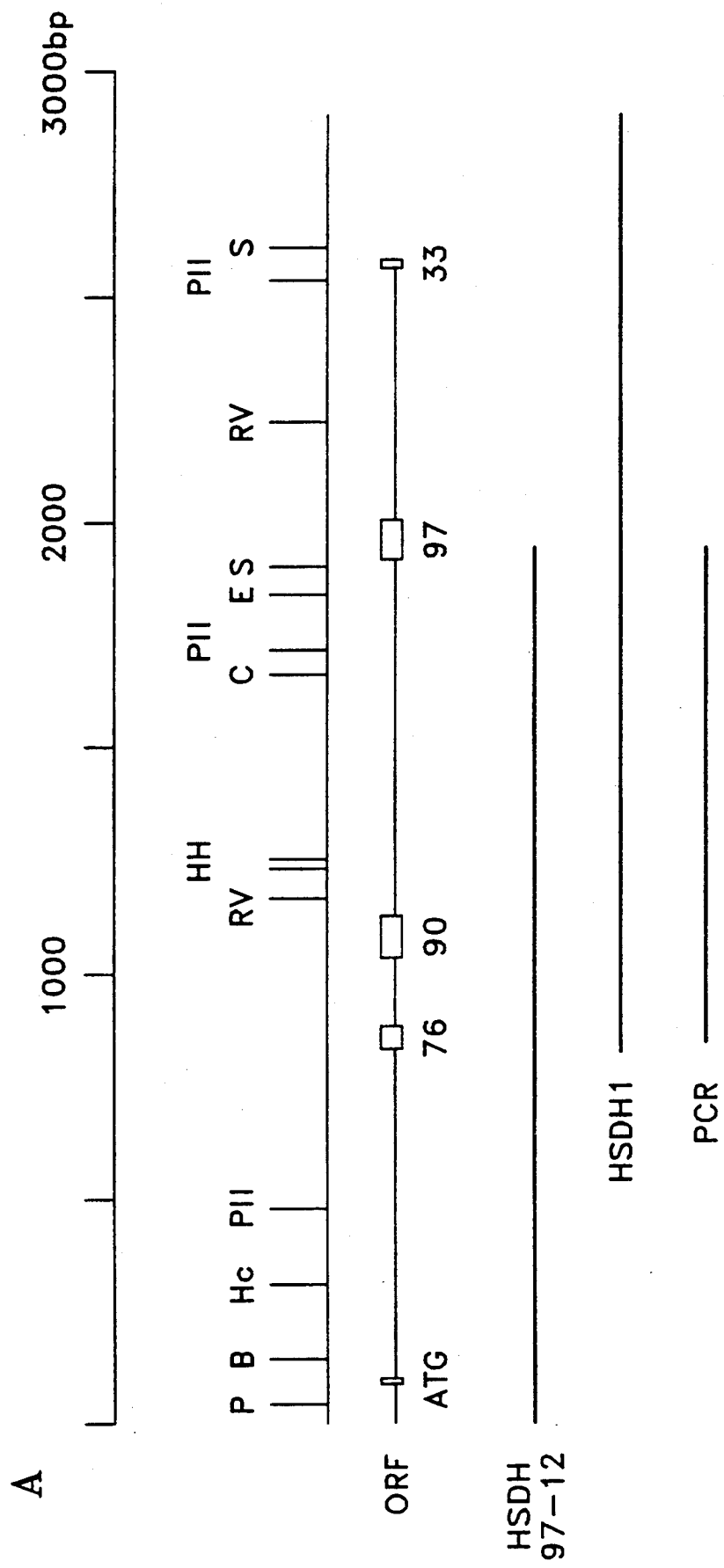
FIG. 7. Map of HSDH clones. Panel A: Restriction map of the full-length HSDH clone (P:PstI; B:BamHI; Hc:HincII; RV:EcoRV; H:HindIII; C:ClaI; E:EcoRI; S:SstI). Shown below this is the location of the 2591bp open reading frame, the potential start codon (ATG), and the positions of the sequenced peptides (76, 90, 97, 33).

FIG. 7 is a map of the HSDH clones. Panel A: Restriction map of the full-length HSDH clone (P:PstI; B:BamHI; Hc:HincII; RV:EcoRV; H:HindIII; C:ClaI; E:EcoRI; S:SstI). Shown below this is the location of the 2591bp open reading frame, the potential start codon (ATG), and the positions of the sequenced peptides (76, 90, 97, 33).

Clone HSDH 1 had no apparent translation start site. RNA blot analysis using the HSDH PCR product as a probe identified a 3000 nucleotide transcript as the main hybridizing band. The open reading frame in the clone was not sufficient to code for a protein of 85,000+/−5000 daltons (the subunit size of the purified carrot enzyme (Matthews (1989), supra). These facts indicated that this clone was lacking approximately 1000bp at the 5' end.

In order to enhance the probability of finding HSDH clones with a complete 5' end a second cDNA library using oligonucleotide HSDH97 to prime first-strand synthesis was constructed. The Poly (A)+ RNA was extracted from carrot cell culture. The cDNA was again cloned into a lambda-gt11 vector. 350,000 plaques were screened and fourteen positive clones were analyzed. Three of these contained inserts that extended beyond the 5' end of HSDH 1. The longest of these clones, HSDH 97-12, was 835bp longer at the 5' end than HSDH1.

Figures 8, 8A, 8B, 8C, 8D, 8E, 8F:
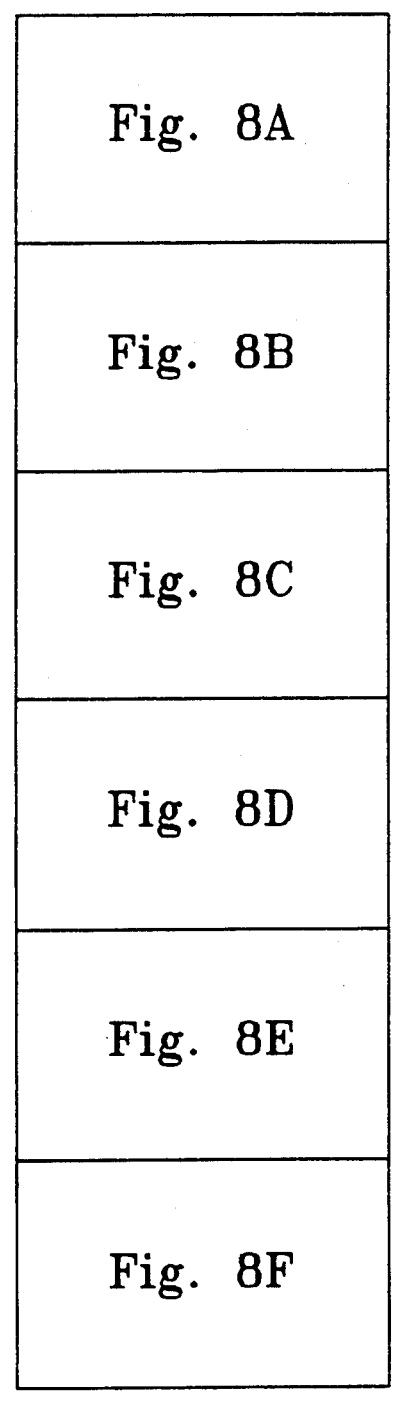

FIG. 8 shows the DNA sequence of carrot AK-HSDH and the deduced amino acid sequence. Also shown are the positions of the peptides whose amino acid sequence was determined.

EXAMPLE VIII

DNA Sequence Analysis and Comparison to Other Genes Coding for HSDH and AK

The DNA sequence was determined for the total length of clones HSDH 1 and HSDH 97-12 and for parts of other clones. FIG. 8 shows the 2915bp DNA sequence of the combined HSDH 1, HSDH 97-12 and other clones and the deduced amino acid sequence for the open reading frame from base pair 2 through base pair 2590. The sequences of four tryptic peptides from the purified carrot HSDH had been previously determined. These were compared to the deduced amino acid sequence from the cDNA clone and are also shown in FIG. 8. Only one amino acid residue out of 92 did not match ([S] in peptide 90) and this one was ambiguous in the peptide sequence.

The amino terminal sequence has not been determined for the carrot HSDH protein. There is a possible translation start site (ATG) at base pair 98 in the clone. If translation were to start at this site, the resulting 831 amino acid protein would have a molecular weight of 90,679 daltons, which is in the expected size range.

The deduced amino acid sequence of the carrot HSDH clone was compared to bacterial and fungal HSDH and AK proteins for which there is sequence information (See Table V). The strongest homology was between the carrot clone and the E. coli thrA gene.

Figure 9:
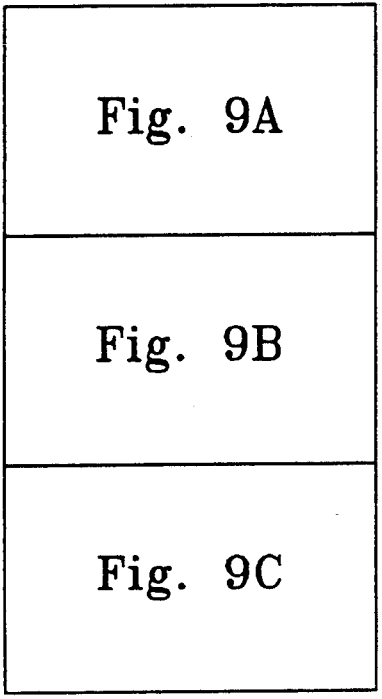
FIG. 9. Comparison of carrot HSDH and *E. coli* AKI-HSDHI. The deduced amino acid sequence of the carrot HSDH was compared to the *E. coli* AKI-HSDHI using the GAP program of the University of Wisconsin Genetics Computer Group. Vertical lines indicate identical amino acids; dots indicate amino acids encoded by similar codons (double dot: codons differing in one nucleotide; single dots: codons differing in two nucleotides). An asterisk (*) under a pair of amino acids indicates identities shared by carrot AK-HSDH, the three *E. coli* proteins, *B. subtilis* AKII and yeast AK, a circle (o) indicates identities shared by the carrot protein, *E. coli* HSDHI and II, *B. subtilis* HSDH and *D. glutamicum* HSDH.

FIG. 9 shows a comparison of carrot HSDH and E. coli AKI-HSDHI. The deduced amino acid sequence of the carrot HSDH was compared to the E. coli AKI-HSDHI using the GAP program of the University of Wisconsin Genetics Computer Group. Vertical lines indicate identical amino acids; dots indicate amino acids encoded by similar codons (double dot: codons differing in one nucleotide; single dots: codons differing in two nucleotides). An asterisk (*) under a pair of amino acids indicates identities shared by carrot AK-HSDH, the three E. coli proteins, B. subtilis AKII and yeast AK, a circle (o) indicates identities shared by the carrot protein, E. coli HSDHI and II, B. subtilis HSDH and D. glutamicum HSDH.

ThrA encodes the E. coli AKI-HSDHI bifunctional aspartokinase-homoserine dehydrogenase protein. E. coli AKI-HSDHI is 820 amino acids long; the amino-terminal 248 amino acids constitute the aspartokinase functional domain, the carboxy-terminal 324 residues constitute the homoserine dehydrogenase domain, and residues from abut 249 to 495 make up a central interface domain (Cohen (1987), supra). AKII-HSDHII has a similar structure. Proteins with only AK function (E. coli AKIII, Bacillus subtilis AKII, yeast AK) have homology to amino acids 1 through 500 of AKI-HSDHI. Proteins with only HSDH function (Bacillus subtilis HSDH, Corynebacterium glutamicum HSDH) have homology beginning at about amino acid 500 and extending through the carboxy-terminus of AKI-HSDHI. There is homology between the carrot HSDH and E. coli AKI-HSDHI along the full length of the proteins, although it is strongest in the HSDH domain and the interface domain. The homology with AKII-HSDHII is at a similar level, except in the interface region, where it is reduced.

TABLE V

Homology between carrot AK-HDSH and AK and HSDH proteins from other organisms.
Comparisons of the carrot AK-HSDH to the three enzymes from E. coli, to the AK of Bacillus subtilis, and to the HSDH from Corynebacterium glutamicum were made using the GAP program of the University of Wisconsin Genetics Computer Group. The comparisons to the B. subtilis HSDH and Saccharomyces cerevisiae AK were based on published alignments between these proteins and the E. coli proteins (C. Parsot, et al., J Biol Chem 263: 14654–60 (1988) and Rafalski, supra).

|  | % | | |
|---|---|---|---|
|  | Identity | Homology[a] | Total Identity + homology |
| E. coli AKI-HSDHI | 38 | 10 | 48 |
| Amino acid 33-282[b] | 30 | 9 | 39 |
| Amino acid 283-489 | 40 | 9 | 49 |
| Amino acid 490-864 | 40 | 10 | 50 |
| E. coli AKII-HSDHII | 33 | 9 | 42 |
| Amino acid 33-282 | 32 | 7 | 39 |
| Amino acid 283-489 | 19 | 9 | 28 |
| Amino acid 490-864 | 38 | 10 | 48 |
| E. coli AKIII (Amino acid 33-500) | 28 | 12 | 40 |
| B. subtilis AKII (Amino acid 33-502) | 33 | 9 | 42 |
| B. subtilis HSDH (Amino acid 502-864) | 22 | 7 | 30 |
| C. glutamicum HSDH (Amino acid 490-864) | 25 | 11 | 36 |
| S. cerevisiae A K (Amino acid 33-405) |  |  |  |

[a]Amino acid replacements: ile—val—leu, ser—thr, lys—arg, phe—tyr, glu—asp.
[b]Amino acid residue numbers refer to the amino acids of the carrot protein as shown in FIG. 9.

All aspartokinases analyzed have the sequence KFGGT near the amino-terminus. This includes the yeast and Bacillus subtilis aspartokinases, E. coli AKIII, and E. coli AKI-HSDHI. E. coli AKII-HSDHII has the variation KFGGS. The deduced amino acid sequence of the carrot HSDH clone also has the KFGGT sequence (amino acids 38-42 in FIG. 9 and underlined in FIG. 8). Another highly conserved region contains the Gly-X-Gly-X-X-Gly motif which is presumed to be part of the NADH/NADPH binding domain of HSDH (C. Parsot, et al., J Biol Chem 263: 14654–60 (1988)). This is found in the carrot sequence at amino acids 512–517 as numbered in FIG. 9.

EXAMPLE IX

DNA and RNA Blot Analysis

All the carrot cDNA clones isolated appeared to represent the same gene. However, it was possible that there were additional genes for AK or HSDH. To test for the existence of other related mRNAs total carrot RNA was probed with the AK-HSDH clone.

Figure 10:
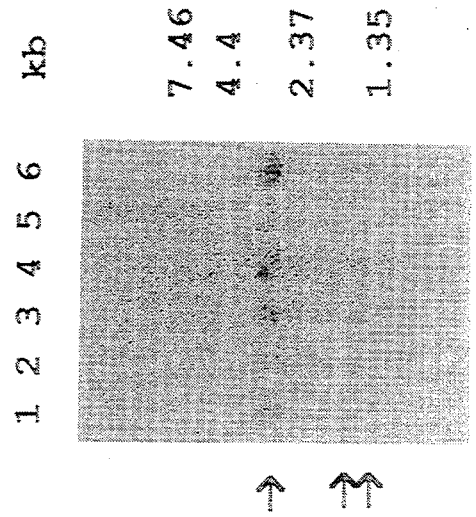
FIG. 10. Northern blot of carrot RNA probed with the HSDH clone. 10 ug of total RNA from each sample was run on an agarose-formaldehyde-formamide gel and transferred to nitrocellulose membrane. The blot was probed with a $^{32}$P-labelled 300 bp EcoRI-HincII fragment from the 5'-end of the clone. Hybridization was in 50% formamide/5×SSPE/5×Denhardt's/0.6% SDS/100 ug/ml denatured salmon sperm DNA at 42"C for 18 hr. The final wash of the blot was in 0.1×SSC/0.1% SDS at 42° C. Lane 1-4: carrot cell culture (lane 1: 1 day; lane 2: 3 days; lane 3: 5 days, lane 4: 7 days and transfer); lane 5: 2 month old leaves; lane 6: 2 month old roots).

FIG. 10 shows a Northern blot of carrot RNA probed with the HSDH clone. 10 ug of total RNA from each sample was run on an agarose-formaldehyde-formamide gel and transferred to nitrocellulose membrane. The blot was probed with a $^{32}$P-labelled 300 bp EcoRI-HincII fragment from the 5'-end of the clone. Hybridization was in 50% formamide/5×SSPE/5×Denhardt's/0.6% SDS/100 ug/ml denatured salmon sperm DNA at 42° C. for 18 hr. The final wash of the blot was in 0.1×SSC/0.1% SDS at 42° C. Lane 1–4: carrot cell culture (lane 1: 1 day; lane 2: 3 days; lane 3: 5 days, lane 4: 7 days and transfer); lane 5: 2 month old leaves; lane 6: 2 month old roots).

The Northern blots showed predominantly a message of about 3000 nucleotides. Minor bands were also seen at about 1500 and 1250 nucleotides. It has not been determined if this is a breakdown product of the larger RNA or a second message. Although FIG. 10 shows a blot probed with a 300bp fragment from the 5'-end of the clone, a similar pattern was seen when the full-length cDNA was used.

Figure 11:
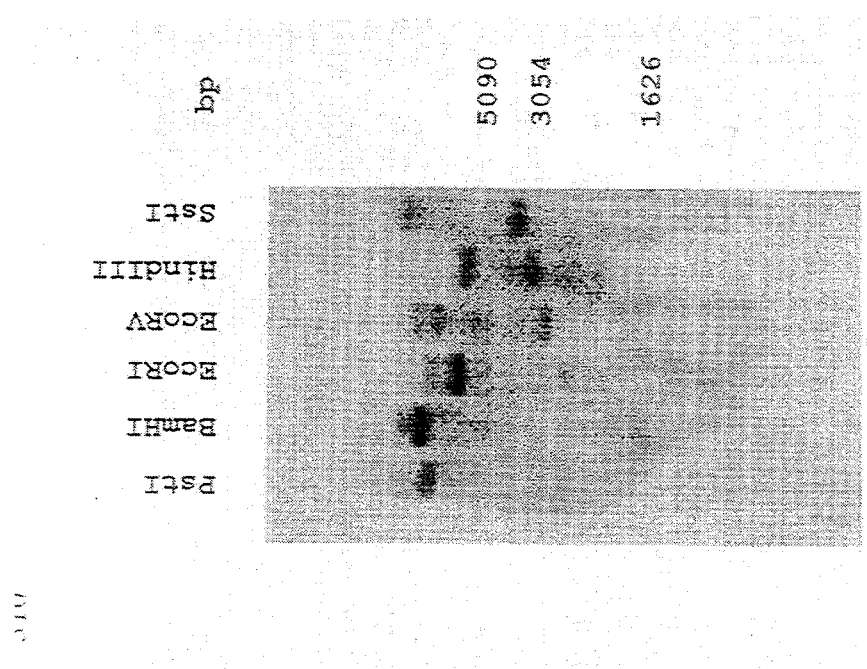
FIG. 11. Southern blot of carrot genomic DNA probed with the HSDH cDNA clone. Carrot leaf DNA was digested with the indicated restricted enzymes, run on an agarose gel and blotted to nitrocellulose membrane. The blot was probed with the full-length HSDH clone. Hybridization was in 25% formamide/5×SSPE/5×Denhardt's/0.5% SDS/100 ug/ml denatured salmon sperm DNA at 42° C. for 23 hr. The final wash of the blot was in 2×SSC/0.2% SDS at 42° C.

Genomic carrot DNA was also probed with the AK-HSDH clone. FIG. 11 shows a Southern blot of carrot genomic DNA probed with the HSDH cDNA clone. Carrot leaf DNA was digested with the indicated restricted enzymes (restriction endonucleases), run on an agarose gel and blotted to nitrocellulose membrane. The blot was probed with the full-length HSDH clone. Hybridization was in 25% formamide/5×SSPE/5×-Denhardt's/0.5% SDS/100 ug/ml denatured salmon sperm DNA at 42° C. for 23 hr. The final wash of the blot was in 2×SSC/0.2% SDS at 42° C.

The blots were probed at low stringency and washed at both low and high temperatures. All the blots revealed fairly simple banding patterns, indicating a low number of hybridizing sequences in the genome. In contrast soybean genomic blots probed with the carrot HSDH clone showed a much more complex pattern. If there were related, but only partially homologous, sequences in the genome, higher wash temperatures should have removed the bands for these sequences preferentially from blots. This did not occur. Higher wash temperatures simply reduced the intensity of all bands.

The references cited above are all incorporated by reference herein, whether specifically incorporated or not.

Having now fully described this invention, it will be appreciated by those skilled in the art that the same can be performed within a wide range of equivalent paramenters, concentrations, and conditions without departing form the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims. It is to be understood that the phraseology or terminology employed herein is for the purpose of description and not of limitation.

What is claimed:

1. A purified and isolated DNA molecule comprising a DNA sequence coding for a homologous segment of bifunctional protein extracted from carrots, wherein said protein segment is a means for regulating the lysine and homoserine content in plants, and wherein said protein segment has both homoserine dehydrogenase and aspartokinase activity.

2. A DNA molecule wherein the DNA sequence has the following nucleotide sequence SEQ ID NO: 16):

3. A polynucleotide molecule comprising:
a first nucleotide sequence encoding a protein according to claim 1,
a second nucleotide sequence heterlogous to said first nucleotide sequence, and
both said sequnces in operable linkage with each other, wherein said polynucleotide molecule encodes at least one protein.

4. A polynucleotide molecule according to claim 2, wherein said first nucleotide sequence is a DNA molecule comprising a DNA sequence coding for a homologous segment of bifunctional protein extracted from carrots, wherein said protein segment is a means for regulating the lysine and homoserine content in plants, and wherein said protein segment has both homoserine dehydrogenase and aspartokinase activity.

5. A polynucleotide molecule according to claim 3, wherein said first nucleotide sequence is a DNA molecule having the sequence of (SEQ ID NO: 16).

6. A polynucletide molecule according to claim 3, wherein said second nucleotide sequence is the bacteriophage lambda gt11.

7. A polynucleotide molecule according to claim 3, which is an expression vehicle.

8. A polynucleotide molecule according to claim 7, wherein said vehicle comprises a replicon, plasmid, bacteriophage, virus or hybrid thereof.

9. A host transformed or transfected with the molecule according to claim 7.

10. A method of producing a purified recombinant bifunctional protein using recombinant cells comprising:
culturing a host according to claim 9, capable of expressing said protein under culturing conditions;
expressing said protein; and
recovering said protein from said culture.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Daucus carota ( x i ) SEQUENCE DESCRIPTION: SEQ ID NO:1:

```
Ser Tyr Thr His Tyr Phe Tyr Glu Ala Thr Val Gly Ala Gly Leu Pro
1               5                   10                  15
    Ile Ile Thr Thr Leu Gln Gly Leu Leu Glu Thr Gly Asp
                20                  25
```

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Escherichia coli ( x i ) SEQUENCE DESCRIPTION: SEQ ID NO:2:

```
Ser Arg Arg Lys Phe Leu Lys Asp Ile Asn Val Gly Ala Gly Leu Pro
1               5                   10                  15
Val Ile Glu Asn Leu Gln Asn Leu Leu Asn Ala Gly Asp
                20                  25
```

( 2 ) INFORMATION FOR SEQ ID NO:3:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Escherichia coli ( x i ) SEQUENCE DESCRIPTION: SEQ ID NO:3:

```
Thr Gly Arg His Trp Leu Tyr Asn Ala Thr Val Gly Ala Gly Leu Pro
1               5                   10                  15
Ile Asn His Thr Val Arg Asp Leu Ile Asp Ser Gly Asp
```

( 2 ) INFORMATION FOR SEQ ID NO:4:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Bacillus subtilis ( x i ) SEQUENCE DESCRIPTION: SEQ ID NO:4:

```
Glu Asn Gly Cys Asp Thr Tyr Phe Glu Ala Ser Val Ala Gly Gly Ile
 1               5                  10                 15

Pro Ile Leu Arg Thr Leu Glu Glu Gly Leu Ser Ser Asp
            20                  25
```

( 2 ) INFORMATION FOR SEQ ID NO:5:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Brevibacterium lactofermentum ( x i ) SEQUENCE DESCRIPTION: SEQ ID NO:5:

```
Asn Val Asp Leu Tyr Phe Glu Ala Ala Val Ala Gly Ala Leu Pro Val
 1               5                  10                 15

Val Gly Pro Leu Arg Arg Ser Leu Ala Gly Asp
            20                  25
```

( 2 ) INFORMATION FOR SEQ ID NO:6:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Daucus carota ( x i ) SEQUENCE DESCRIPTION: SEQ ID NO:6:

```
Thr Leu Asp Tyr Gln Glu Ala Trp Glu Met Ser Tyr Phe Gly Ala Asn
 1               5                  10                 15

Val Leu His Pro Arg
            20
```

( 2 ) INFORMATION FOR SEQ ID NO:7:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( v ) FRAGMENT TYPE: internal (v i) ORIGINAL SOURCE:
    (A) ORGANISM: Escherichia coli (x i) SEQUENCE DESCRIPTION: SEQ ID NO:7:

Ser Met Ser Tyr Gln Glu Ala Met Glu Leu Ser Tyr Phe Gly Ala Lys
1               5                   10                  15
Val Leu His Pro Arg
            20

(2) INFORMATION FOR SEQ ID NO:8:

(i) SEQUENCE CHARACTERISTICS:
        (A) LENGTH: 21 amino acids
        (B) TYPE: amino acid
        (D) TOPOLOGY: linear (i i) MOLECULE TYPE: peptide (v) FRAGMENT TYPE: internal (v i) ORIGINAL SOURCE:
        (A) ORGANISM: Escherichia coli (x i) SEQUENCE DESCRIPTION: SEQ ID NO:8:

Leu Leu Arg Leu Asp Glu Ala Ser Glu Leu Ala Arg Leu Ala Ala Pro
1               5                   10                  15
Val Leu His Ala Arg
            20

(2) INFORMATION FOR SEQ ID NO:9:

(i) SEQUENCE CHARACTERISTICS:
        (A) LENGTH: 21 amino acids
        (B) TYPE: amino acid
        (D) TOPOLOGY: linear (i i) MOLECULE TYPE: peptide (v) FRAGMENT TYPE: internal (v i) ORIGINAL SOURCE:
        (A) ORGANISM: Escherichia coli (x i) SEQUENCE DESCRIPTION: SEQ ID NO:9:

Glu Ile Ala Phe Ala Glu Ala Ala Phe Met Ala Thr Phe Gly Ala Lys
1               5                   10                  15
Val Leu His Pro Ala
            20

(2) INFORMATION FOR SEQ ID NO:10:

(i) SEQUENCE CHARACTERISTICS:
        (A) LENGTH: 21 amino acids
        (B) TYPE: amino acid
        (D) TOPOLOGY: linear (i i) MOLECULE TYPE: peptide (v) FRAGMENT TYPE: internal (v i) ORIGINAL SOURCE:
        (A) ORGANISM: Bacillus subtilis (x i) SEQUENCE DESCRIPTION: SEQ ID NO:10:

Gly Ile Ser Tyr Asp Glu Met Leu Glu Leu Ala Asn Leu Gly Ala Gly
1               5                   10                  15
Val Leu His Pro Arg
            20

( 2 ) INFORMATION FOR SEQ ID NO:11:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:11:

```
Ser Val Thr Pro Glu Glu Ala Ser Glu Leu Thr Tyr Tyr Gly Ser Glu
1               5                   10                  15
Val Ile His Pro Phe
            20
```

( 2 ) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:12:

```
GCYTCRTARA ARTARTGNGT RTA                                        23
```

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:13:

```
TAYCARGARG CNTGGGARAT G                                          21
```

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Daucus carota ( x i ) SEQUENCE DESCRIPTION: SEQ ID NO:14:

```
Tyr Gln Glu Ala Trp Glu Met
1               5
```

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide (v) FRAGMENT TYPE: internal (vi) ORIGINAL SOURCE:
  (A) ORGANISM: Daucus carota (xi) SEQUENCE DESCRIPTION: SEQ ID NO:15:

Tyr Thr His Tyr Phe Tyr Glu Ala
1               5

(2) INFORMATION FOR SEQ ID NO:16:

(i) SEQUENCE CHARACTERISTICS:
    (A) LENGTH: 2915 base pairs
    (B) TYPE: nucleic acid
    (C) STRANDEDNESS: both
    (D) TOPOLOGY: linear (ii) MOLECULE TYPE: cDNA to mRNA (iii) HYPOTHETICAL: NO (iv) ANTI-SENSE: NO (ix) FEATURE:
    (A) NAME/KEY: CDS
    (B) LOCATION: 2..2593

(xi) SEQUENCE DESCRIPTION: SEQ ID NO:16:

| | | | | | | | | | | | | | | | | |
|---|---|---|---|---|---|---|---|---|---|---|---|---|---|---|---|---|
| G | GAG | TCG | TCG | TCG | AAG | TTT | TAC | ATT | GCT | GCT | TCC | GTT | ACA | ACT | GCA | 46 |
|   | Glu | Ser | Ser | Ser | Lys | Phe | Tyr | Ile | Ala | Ala | Ser | Val | Thr | Thr | Ala |   |
|   | 1   |     |     |     | 5   |     |     |     |     | 10  |     |     |     |     | 15  |   |
| GTT | CCT | TCT | CTC | GAT | GAC | TCC | GTT | GAG | AAG | GTT | CAC | CTT | CCC | AGG | GGT | 94 |
| Val | Pro | Ser | Leu | Asp | Asp | Ser | Val | Glu | Lys | Val | His | Leu | Pro | Arg | Gly |   |
|     |     |     | 20  |     |     |     |     | 25  |     |     |     |     | 30  |     |     |   |
| GCT | ATG | TGG | TCT | ATT | CAT | AAA | TTT | GGA | GGC | ACC | TGT | GTG | GGA | AGC | TCT | 142 |
| Ala | Met | Trp | Ser | Ile | His | Lys | Phe | Gly | Gly | Thr | Cys | Val | Gly | Ser | Ser |   |
|     |     |     | 35  |     |     |     |     | 40  |     |     |     |     | 45  |     |     |   |
| GAA | AGG | ATC | CGA | AAT | GTT | GCA | GAG | ATA | GTT | GTG | GAG | GAT | GAT | TCT | GAA | 190 |
| Glu | Arg | Ile | Arg | Asn | Val | Ala | Glu | Ile | Val | Val | Glu | Asp | Asp | Ser | Glu |   |
|     |     |     | 50  |     |     |     |     | 55  |     |     |     |     | 60  |     |     |   |
| AGA | AAG | CTA | GTT | GTA | GTC | TCT | GCA | ATG | TCA | AAG | GTC | ACA | GAT | ATG | ATG | 238 |
| Arg | Lys | Leu | Val | Val | Val | Ser | Ala | Met | Ser | Lys | Val | Thr | Asp | Met | Met |   |
|     | 65  |     |     |     |     | 70  |     |     |     |     | 75  |     |     |     |     |   |
| TAT | GAT | CTA | ATT | TAC | AAG | GCG | CAG | TCA | CGG | GAT | GAT | TCT | TAT | GAA | TCT | 286 |
| Tyr | Asp | Leu | Ile | Tyr | Lys | Ala | Gln | Ser | Arg | Asp | Asp | Ser | Tyr | Glu | Ser |   |
| 80  |     |     |     |     | 85  |     |     |     |     | 90  |     |     |     |     | 95  |   |
| GCG | CTC | GAT | GCT | GTT | ATG | GAA | AAG | CAC | AAG | TTA | ACA | GCA | TTT | GAT | CTC | 334 |
| Ala | Leu | Asp | Ala | Val | Met | Glu | Lys | His | Lys | Leu | Thr | Ala | Phe | Asp | Leu |   |
|     |     |     |     | 100 |     |     |     |     | 105 |     |     |     |     | 110 |     |   |
| CTT | GAT | GGA | GAT | GAC | CTT | GCT | AGA | TTT | TTA | ACT | AGG | CTG | CAA | CAT | GAT | 382 |
| Leu | Asp | Gly | Asp | Asp | Leu | Ala | Arg | Phe | Leu | Thr | Arg | Leu | Gln | His | Asp |   |
|     |     |     | 115 |     |     |     |     | 120 |     |     |     |     | 125 |     |     |   |
| GTT | AAT | AAC | CTC | AAA | GCA | ATG | CTT | CGT | GCA | ATA | TAC | ATA | GCT | GGT | CAT | 430 |
| Val | Asn | Asn | Leu | Lys | Ala | Met | Leu | Arg | Ala | Ile | Tyr | Ile | Ala | Gly | His |   |
|     |     |     | 130 |     |     |     |     | 135 |     |     |     |     | 140 |     |     |   |
| GCC | ACC | GAA | TCT | TTT | TCG | GAT | TTT | GTT | GTG | GGA | CAT | GGA | GAG | CTA | TGG | 478 |
| Ala | Thr | Glu | Ser | Phe | Ser | Asp | Phe | Val | Val | Gly | His | Gly | Glu | Leu | Trp |   |
|     |     |     | 145 |     |     |     |     | 150 |     |     |     |     | 155 |     |     |   |
| TCA | GCT | CAG | CTG | TTG | TCA | TTT | GTA | ATA | AGA | AAG | AAT | GGG | GGT | GAC | TGT | 526 |
| Ser | Ala | Gln | Leu | Leu | Ser | Phe | Val | Ile | Arg | Lys | Asn | Gly | Gly | Asp | Cys |   |
| 160 |     |     |     |     | 165 |     |     |     |     | 170 |     |     |     |     | 175 |   |
| AAT | TGG | ATG | GAC | ACA | CGA | GAT | GTT | CTT | GTT | GTA | AAT | CCT | GCT | GGA | TCT | 574 |
| Asn | Trp | Met | Asp | Thr | Arg | Asp | Val | Leu | Val | Val | Asn | Pro | Ala | Gly | Ser |   |
|     |     |     |     | 180 |     |     |     |     | 185 |     |     |     |     | 190 |     |   |
| AAT | CAA | GTC | GAT | CCT | GAT | TAT | TTG | GAA | TCT | GAG | AAG | AGA | CTT | GAG | AAA | 622 |
| Asn | Gln | Val | Asp | Pro | Asp | Tyr | Leu | Glu | Ser | Glu | Lys | Arg | Leu | Glu | Lys |   |

|     |     |     |     |     |     |     |     |     |     |     |     |     |     |     |     |
| --- | --- | --- | --- | --- | --- | --- | --- | --- | --- | --- | --- | --- | --- | --- | --- |
|     |     | 195 |     |     |     |     | 200 |     |     |     |     | 205 |     |     |     |
| TGG | TTC | TCC | AGC | AAC | CAG | TGT | CAG | ACA | ATT | GTT | GCG | ACA | GGT | TTT | ATA | 670 |
| Trp | Phe | Ser | Ser | Asn | Gln | Cys | Gln | Thr | Ile | Val | Ala | Thr | Gly | Phe | Ile |
|     |     | 210 |     |     |     | 215 |     |     |     |     | 220 |     |     |     |     |
| GCT | AGC | ACG | CCT | CAA | AAT | ATA | CCT | ACA | ACT | TTG | AAA | AGA | GAC | GGA | AGT | 718 |
| Ala | Ser | Thr | Pro | Gln | Asn | Ile | Pro | Thr | Thr | Leu | Lys | Arg | Asp | Gly | Ser |
|     | 225 |     |     |     |     | 230 |     |     |     |     | 235 |     |     |     |     |
| GAC | TTT | TCT | GCC | GCT | ATA | ATG | GGT | GCT | TTA | TTA | AGG | GCT | GGT | CAA | GTC | 766 |
| Asp | Phe | Ser | Ala | Ala | Ile | Met | Gly | Ala | Leu | Leu | Arg | Ala | Gly | Gln | Val |
| 240 |     |     |     |     | 245 |     |     |     |     | 250 |     |     |     |     | 255 |
| ACG | ATT | TGG | ACT | GAT | GTT | AAT | GGT | GTA | TAT | AGT | GCA | GAT | CCT | CGA | AAA | 814 |
| Thr | Ile | Trp | Thr | Asp | Val | Asn | Gly | Val | Tyr | Ser | Ala | Asp | Pro | Arg | Lys |
|     |     |     |     | 260 |     |     |     |     | 265 |     |     |     |     | 270 |     |
| GTT | AGT | GAG | GCT | GTG | GTA | TTA | AAG | ACA | TTG | TCT | TAT | CAA | GAA | GCC | TGG | 862 |
| Val | Ser | Glu | Ala | Val | Val | Leu | Lys | Thr | Leu | Ser | Tyr | Gln | Glu | Ala | Trp |
|     |     |     |     | 275 |     |     |     |     | 280 |     |     |     |     | 285 |     |
| GAG | ATG | TCA | TAT | TTT | GGG | GCT | AAT | GTG | TTA | CAT | CCC | CGT | ACT | ATC | ATT | 910 |
| Glu | Met | Ser | Tyr | Phe | Gly | Ala | Asn | Val | Leu | His | Pro | Arg | Thr | Ile | Ile |
|     |     | 290 |     |     |     |     | 295 |     |     |     |     | 300 |     |     |     |
| CCT | GTG | ATG | CGA | TAT | GAC | ATT | CCA | ATT | GTA | ATA | AGA | AAT | ATA | TTC | AAC | 958 |
| Pro | Val | Met | Arg | Tyr | Asp | Ile | Pro | Ile | Val | Ile | Arg | Asn | Ile | Phe | Asn |
|     | 305 |     |     |     |     | 310 |     |     |     |     | 315 |     |     |     |     |
| CTA | TCT | GCT | CCG | GGA | ACA | ATG | ATA | TGC | CGA | GAA | TCT | GTA | GGC | GAA | ACT | 1006 |
| Leu | Ser | Ala | Pro | Gly | Thr | Met | Ile | Cys | Arg | Glu | Ser | Val | Gly | Glu | Thr |
| 320 |     |     |     |     | 325 |     |     |     |     | 330 |     |     |     |     | 335 |
| GAA | GAT | GGG | TTA | AAA | TTG | GAA | TCT | CAT | GTC | AAA | GGA | TTT | GCT | ACT | ATT | 1054 |
| Glu | Asp | Gly | Leu | Lys | Leu | Glu | Ser | His | Val | Lys | Gly | Phe | Ala | Thr | Ile |
|     |     |     |     | 340 |     |     |     |     | 345 |     |     |     |     | 350 |     |
| GAT | AAT | CTG | GCG | CTC | ATT | AAT | GTT | GAA | GGA | ACT | GGA | ATG | GCT | GGT | GTT | 1102 |
| Asp | Asn | Leu | Ala | Leu | Ile | Asn | Val | Glu | Gly | Thr | Gly | Met | Ala | Gly | Val |
|     |     |     | 355 |     |     |     |     | 360 |     |     |     |     | 365 |     |     |
| CCT | GGT | ACA | GCT | AGT | GCA | ATT | TTT | GGT | GCT | GTC | AAG | GAT | GTG | GGA | GCT | 1150 |
| Pro | Gly | Thr | Ala | Ser | Ala | Ile | Phe | Gly | Ala | Val | Lys | Asp | Val | Gly | Ala |
|     |     | 370 |     |     |     |     | 375 |     |     |     |     | 380 |     |     |     |
| AAT | GTT | ATA | ATG | ATA | TCT | CAG | GCT | AGC | AGT | GAG | CAT | TCT | ATT | TGC | TTT | 1198 |
| Asn | Val | Ile | Met | Ile | Ser | Gln | Ala | Ser | Ser | Glu | His | Ser | Ile | Cys | Phe |
|     | 385 |     |     |     |     | 390 |     |     |     |     | 395 |     |     |     |     |
| GCT | GTG | CCT | GAG | AGT | GAA | GTG | AAA | GCT | GTT | GCT | AAA | GCT | TTG | GAG | GCC | 1246 |
| Ala | Val | Pro | Glu | Ser | Glu | Val | Lys | Ala | Val | Ala | Lys | Ala | Leu | Glu | Ala |
| 400 |     |     |     |     | 405 |     |     |     |     | 410 |     |     |     |     | 415 |
| AGA | TTT | CGT | CAA | GCT | TTA | GAT | GCT | GGT | CGT | CTT | TCC | CAG | GTT | GCT | ATT | 1294 |
| Arg | Phe | Arg | Gln | Ala | Leu | Asp | Ala | Gly | Arg | Leu | Ser | Gln | Val | Ala | Ile |
|     |     |     |     | 420 |     |     |     |     | 425 |     |     |     |     | 430 |     |
| ATT | CCA | AAC | TGT | AGC | ATC | TTG | GCA | ACA | GTT | GGC | CAA | AAG | ATG | GCA | AGT | 1342 |
| Ile | Pro | Asn | Cys | Ser | Ile | Leu | Ala | Thr | Val | Gly | Gln | Lys | Met | Ala | Ser |
|     |     |     | 435 |     |     |     |     | 440 |     |     |     |     | 445 |     |     |
| ACT | CCT | GGC | GTG | AGT | GCT | ACA | CTT | TTC | AAT | GCG | CTT | GCA | AAG | GCC | AAT | 1390 |
| Thr | Pro | Gly | Val | Ser | Ala | Thr | Leu | Phe | Asn | Ala | Leu | Ala | Lys | Ala | Asn |
|     |     | 450 |     |     |     |     | 455 |     |     |     |     | 460 |     |     |     |
| ATA | AAC | GTT | CGT | GCT | ATA | GCC | CAG | GGC | TGT | ACA | GAG | TAT | AAT | ATC | ACT | 1438 |
| Ile | Asn | Val | Arg | Ala | Ile | Ala | Gln | Gly | Cys | Thr | Glu | Tyr | Asn | Ile | Thr |
|     | 465 |     |     |     |     | 470 |     |     |     |     | 475 |     |     |     |     |
| GTA | GTT | CTC | AGT | CGA | GAA | GAT | TGT | GTG | AGG | GCT | TTG | AAA | GCT | GTC | CAT | 1486 |
| Val | Val | Leu | Ser | Arg | Glu | Asp | Cys | Val | Arg | Ala | Leu | Lys | Ala | Val | His |
| 480 |     |     |     |     | 485 |     |     |     |     | 490 |     |     |     |     | 495 |
| TCA | AGA | TTT | TAT | CTG | TCG | AGA | ACC | ACA | ATA | GCA | GTG | GGT | ATT | GTC | GGA | 1534 |
| Ser | Arg | Phe | Tyr | Leu | Ser | Arg | Thr | Thr | Ile | Ala | Val | Gly | Ile | Val | Gly |
|     |     |     |     | 500 |     |     |     |     | 505 |     |     |     |     | 510 |     |
| CCT | GGA | TTA | ATC | GGA | GCT | ACT | TTA | CTT | GAC | CAG | CTC | AGG | GAT | CAG | GCA | 1582 |
| Pro | Gly | Leu | Ile | Gly | Ala | Thr | Leu | Leu | Asp | Gln | Leu | Arg | Asp | Gln | Ala |
|     |     |     | 515 |     |     |     |     | 520 |     |     |     |     | 525 |     |     |

| | | | | | | | | | | | | | | | | |
|---|---|---|---|---|---|---|---|---|---|---|---|---|---|---|---|---|
| GCA | ATC | CTC | AAG | GAA | AAT | TCT | AAA | ATT | GAT | TTG | CGT | GTT | ATG | GGT | ATC | 1630 |
| Ala | Ile | Leu | Lys | Glu | Asn | Ser | Lys | Ile | Asp | Leu | Arg | Val | Met | Gly | Ile | |
| | | 530 | | | | 535 | | | | | 540 | | | | | |
| ACC | GGA | TCG | AGA | ACA | ATG | CTT | CTG | AGC | GAA | ACG | GGA | ATC | GAT | TTA | AGT | 1678 |
| Thr | Gly | Ser | Arg | Thr | Met | Leu | Leu | Ser | Glu | Thr | Gly | Ile | Asp | Leu | Ser | |
| | 545 | | | | 550 | | | | | 555 | | | | | | |
| AGA | TGG | AGA | GAA | GTC | CAA | AAA | GAG | AAA | GGG | CAA | ACA | GCT | GGC | CTA | GAA | 1726 |
| Arg | Trp | Arg | Glu | Val | Gln | Lys | Glu | Lys | Gly | Gln | Thr | Ala | Gly | Leu | Glu | |
| 560 | | | | 565 | | | | | 570 | | | | | | 575 | |
| AAA | TTT | GTA | CAA | CAT | GTG | CGT | GGA | AAT | CAT | TTT | ATT | CCA | AGC | ACT | GTT | 1774 |
| Lys | Phe | Val | Gln | His | Val | Arg | Gly | Asn | His | Phe | Ile | Pro | Ser | Thr | Val | |
| | | | | 580 | | | | | 585 | | | | | 590 | | |
| ATA | GTA | GAT | TGT | ACA | GCA | GAC | TCT | GAA | GTG | GCA | AGT | CAC | TAC | CAT | GAC | 1822 |
| Ile | Val | Asp | Cys | Thr | Ala | Asp | Ser | Glu | Val | Ala | Ser | His | Tyr | His | Asp | |
| | | | 595 | | | | | 600 | | | | | 605 | | | |
| TGG | TTG | TGT | AGG | GGA | ATT | CAC | GTC | ATT | ACC | CCA | AAT | AAG | AAG | GCA | AAT | 1870 |
| Trp | Leu | Cys | Arg | Gly | Ile | His | Val | Ile | Thr | Pro | Asn | Lys | Lys | Ala | Asn | |
| | | 610 | | | | | 615 | | | | | 620 | | | | |
| TCA | GGA | CCC | CTT | GAT | CAG | TAT | TTG | AAG | TTG | AGA | GCT | CTC | CAG | CGG | CGA | 1918 |
| Ser | Gly | Pro | Leu | Asp | Gln | Tyr | Leu | Lys | Leu | Arg | Ala | Leu | Gln | Arg | Arg | |
| | 625 | | | | | 630 | | | | | 635 | | | | | |
| TCC | TAT | ACA | CAC | TAT | TTC | TAT | GAA | GCT | ACT | GTT | GGT | GCT | GGT | CTC | CCG | 1966 |
| Ser | Tyr | Thr | His | Tyr | Phe | Tyr | Glu | Ala | Thr | Val | Gly | Ala | Gly | Leu | Pro | |
| 640 | | | | | 645 | | | | | 650 | | | | | 655 | |
| ATC | ATA | ACC | ACT | TTG | CAG | GGA | CTT | CTT | GAA | ACC | GGG | GAC | AAG | ATA | TTG | 2014 |
| Ile | Ile | Thr | Thr | Leu | Gln | Gly | Leu | Leu | Glu | Thr | Gly | Asp | Lys | Ile | Leu | |
| | | | | 660 | | | | | 665 | | | | | 670 | | |
| CGA | ATT | GAA | GGC | ATT | TTC | AGT | GGG | ACT | CTT | AGT | TAC | ATA | TTC | AAC | AAC | 2062 |
| Arg | Ile | Glu | Gly | Ile | Phe | Ser | Gly | Thr | Leu | Ser | Tyr | Ile | Phe | Asn | Asn | |
| | | | | 675 | | | | | 680 | | | | | 685 | | |
| TTT | AAG | AGT | ACA | ACA | CCT | TTT | AGT | GAA | GTG | GTA | AGT | AGA | GCA | AAA | GCG | 2110 |
| Phe | Lys | Ser | Thr | Thr | Pro | Phe | Ser | Glu | Val | Val | Ser | Arg | Ala | Lys | Ala | |
| | | | 690 | | | | | 695 | | | | | 700 | | | |
| GCA | GGG | TAT | ACT | GAA | CCA | GAT | CCA | AGG | GAT | GAT | CTA | GCC | GGA | ACT | GAT | 2158 |
| Ala | Gly | Tyr | Thr | Glu | Pro | Asp | Pro | Arg | Asp | Asp | Leu | Ala | Gly | Thr | Asp | |
| | 705 | | | | | 710 | | | | | 715 | | | | | |
| GTT | GCT | AGA | AAG | GTA | ATA | ATT | CTT | GCT | AGA | GAA | TCT | GGA | TTA | AAG | CTC | 2206 |
| Val | Ala | Arg | Lys | Val | Ile | Ile | Leu | Ala | Arg | Glu | Ser | Gly | Leu | Lys | Leu | |
| 720 | | | | 725 | | | | | 730 | | | | | | 735 | |
| GAA | CTG | TCT | GAT | ATC | CCT | GTA | CAG | AGC | CTT | GTT | CCA | GAA | CCA | CTA | AGG | 2254 |
| Glu | Leu | Ser | Asp | Ile | Pro | Val | Gln | Ser | Leu | Val | Pro | Glu | Pro | Leu | Arg | |
| | | | | 740 | | | | | 745 | | | | | 750 | | |
| GGT | ATT | GCG | TCA | GCC | GAA | GAA | TTT | CTG | CTA | CAG | CTA | CCA | CAG | TTT | GAT | 2302 |
| Gly | Ile | Ala | Ser | Ala | Glu | Glu | Phe | Leu | Leu | Gln | Leu | Pro | Gln | Phe | Asp | |
| | | | 755 | | | | | 760 | | | | | 765 | | | |
| TCA | GAT | ATG | ACC | AGA | AAA | CGA | GAG | GAT | GCT | GAA | AAT | GCA | GGG | GAA | GTT | 2350 |
| Ser | Asp | Met | Thr | Arg | Lys | Arg | Glu | Asp | Ala | Glu | Asn | Ala | Gly | Glu | Val | |
| | | 770 | | | | | 775 | | | | | 780 | | | | |
| CTA | AGG | TAC | GTT | GGG | GTG | GTG | GAT | GCC | GTA | AAT | CAA | AAA | GGT | GTT | GTT | 2398 |
| Leu | Arg | Tyr | Val | Gly | Val | Val | Asp | Ala | Val | Asn | Gln | Lys | Gly | Val | Val | |
| | 785 | | | | | 790 | | | | | 795 | | | | | |
| GAA | TTG | AAA | AGA | TAC | AAG | AAA | GAG | CAC | CCG | TTC | GCA | CAG | CTT | TCT | GGG | 2446 |
| Glu | Leu | Lys | Arg | Tyr | Lys | Lys | Glu | His | Pro | Phe | Ala | Gln | Leu | Ser | Gly | |
| 800 | | | | | 805 | | | | | 810 | | | | | 815 | |
| TCC | GAT | AAC | ATC | ATT | GCT | TTC | ACA | ACT | GAA | AGA | TAC | AAC | AAG | CAA | CCT | 2494 |
| Ser | Asp | Asn | Ile | Ile | Ala | Phe | Thr | Thr | Glu | Arg | Tyr | Asn | Lys | Gln | Pro | |
| | | | | 820 | | | | | 825 | | | | | 830 | | |
| CTT | ATA | ATT | CGA | GGT | CCT | GGT | GCT | GGG | GCA | GAG | GTG | ACA | GCT | GGT | GGA | 2542 |
| Leu | Ile | Ile | Arg | Gly | Pro | Gly | Ala | Gly | Ala | Glu | Val | Thr | Ala | Gly | Gly | |
| | | | 835 | | | | | 840 | | | | | 845 | | | |
| GTA | TTC | AGT | GAT | ATT | TTG | CGG | CTT | GCT | TCA | TAT | CTT | GGT | GCA | CCA | TCA | 2590 |
| Val | Phe | Ser | Asp | Ile | Leu | Arg | Leu | Ala | Ser | Tyr | Leu | Gly | Ala | Pro | Ser | |

|  | 850 | 855 | 860 |  |  |
|---|---|---|---|---|---|
| TAATCCATTA | GTTGAGCTCT | CAATGTTTTA | CCCTTTGTCA | GCCCAAATTA | TGTTATAGAA | 2650 |
| TTTAGGGAGC | TTTTGCCTAT | TATTAGGTTA | GTATCAAAAC | ATTCTTCTAC | GCTGCATAAG | 2710 |
| AGAACACTTC | ATGCAATTTG | GGTTTCTTTA | GTGGCTTTCT | AGCCAACCCA | AATGTGTCAT | 2770 |
| AGTCTCCACG | ATGCAGAGTT | GATAGAATTG | TTACAAGGGG | ATGTATTATA | GAACCAAGCC | 2830 |
| AATTAAACGG | TGTATCCTTA | TTTGGTAAGG | GATAACGTAT | TAATAATGCC | AAAGTGTTGT | 2890 |
| AACATCTTTT | GTTGCGAATA | AATTT |  |  |  | 2915 |